(12) United States Patent
Bodecker et al.

(10) Patent No.: US 7,931,597 B2
(45) Date of Patent: *Apr. 26, 2011

(54) ANCHORED IMPLANTABLE PRESSURE MONITOR

(75) Inventors: Volker Bodecker, Hannover (DE); Max Georg Ostermeier, Hannover (DE); Stefan Meyer, Breidenbach (DE); Axel Niemeyer, Bielefeld (DE)

(73) Assignee: Vital Sensors Holding Company, Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,978

(22) Filed: Mar. 15, 2010

(65) Prior Publication Data

US 2010/0174201 A1    Jul. 8, 2010

Related U.S. Application Data

(63) Continuation of application No. 11/515,915, filed on Sep. 6, 2006, now Pat. No. 7,682,313.

(51) Int. Cl.
*A61B 5/02* (2006.01)

(52) U.S. Cl. ........ 600/486; 600/485; 600/488; 600/374; 600/375

(58) Field of Classification Search .................. 600/309, 600/316, 322, 327, 332, 333, 354, 373, 486, 600/578
See application file for complete search history.

(56) References Cited

U.S. PATENT DOCUMENTS

| | | | |
|---|---|---|---|
| 3,088,323 A | 5/1963 | Welkowitz et al. |
| 3,672,352 A | 6/1972 | Summers |
| 4,237,900 A | 12/1980 | Schulman et al. |
| 4,274,423 A | 6/1981 | Mizuno et al. |
| 4,556,063 A | 12/1985 | Thompson et al. |
| 4,741,339 A | 5/1988 | Harrison et al. |
| 4,846,191 A | 7/1989 | Brockway et al. |
| 4,897,360 A | 1/1990 | Guckel et al. |
| 4,899,758 A | 2/1990 | Finkelstein et al. |
| 4,996,082 A | 2/1991 | Guckel et al. |
| 5,085,223 A | 2/1992 | Lars et al. |
| 5,113,869 A | 5/1992 | Nappholz et al. |
| 5,195,375 A | 3/1993 | Tenerz et al. |
| 5,231,996 A | 8/1993 | Bardy et al. |
| 5,314,453 A | 5/1994 | Jeutter |
| 5,321,989 A | 6/1994 | Zimmer et al. |
| 5,342,408 A | 8/1994 | deCoriolis et al. |
| 5,358,514 A | 10/1994 | Schulman et al. |
| 5,417,222 A | 5/1995 | Dempsey et al. |
| 5,431,057 A | 7/1995 | Zimmer et al. |
| 5,466,246 A | 11/1995 | Silvian |

(Continued)

FOREIGN PATENT DOCUMENTS

CA      2433049      7/2002

(Continued)

OTHER PUBLICATIONS

Kenneth Ouriel, "Role of Intrasac Pressure Measurements After EVAR: Can They be Followed Noninvasively?," Combined Session: Vascular Surgery and Interventional Radiology, VII 4.1, published no later than Sep. 30, 2003.

(Continued)

*Primary Examiner* — Patricia C Mallari
*Assistant Examiner* — Michael D'Angelo
(74) *Attorney, Agent, or Firm* — Scott E. Kamholz; Foley Hoag LLP

(57) ABSTRACT

An anchored implantable pressure monitor.

19 Claims, 22 Drawing Sheets

U.S. PATENT DOCUMENTS

| | | |
|---|---|---|
| 5,535,752 A | 7/1996 | Halperin et al. |
| 5,564,434 A | 10/1996 | Halperin et al. |
| 5,579,775 A | 12/1996 | Dempsey et al. |
| 5,626,630 A | 5/1997 | Markowitz et al. |
| 5,652,570 A | 7/1997 | Lepkofker |
| 5,704,352 A | 1/1998 | Tremblay et al. |
| 5,759,199 A | 6/1998 | Snell et al. |
| 5,833,603 A | 11/1998 | Kovacs et al. |
| 5,871,627 A | 2/1999 | Abraham-Fuchs et al. |
| 5,919,214 A | 7/1999 | Ciciarelli et al. |
| 5,957,854 A | 9/1999 | Besson et al. |
| 6,015,386 A | 1/2000 | Kensey et al. |
| 6,019,728 A | 2/2000 | Iwata et al. |
| 6,019,729 A | 2/2000 | Itoigawa et al. |
| 6,083,174 A | 7/2000 | Brehmeier-Flick et al. |
| 6,113,533 A | 9/2000 | Howes et al. |
| 6,140,144 A * | 10/2000 | Najafi et al. .................. 438/53 |
| 6,155,267 A | 12/2000 | Nelson |
| 6,159,156 A | 12/2000 | Van Bockel |
| 6,167,312 A | 12/2000 | Goedeke |
| 6,169,925 B1 | 1/2001 | Villaseca et al. |
| 6,186,962 B1 | 2/2001 | Lloyd et al. |
| 6,201,980 B1 | 3/2001 | Darrow et al. |
| 6,206,835 B1 | 3/2001 | Spillman, Jr. et al. |
| 6,295,473 B1 | 9/2001 | Rosar |
| 6,328,699 B1 | 12/2001 | Eigler et al. |
| 6,331,163 B1 | 12/2001 | Kaplan |
| 6,409,674 B1 | 6/2002 | Brockway et al. |
| 6,443,893 B1 | 9/2002 | Schnakenberg et al. |
| 6,454,707 B1 | 9/2002 | Casscells, III et al. |
| 6,454,720 B1 | 9/2002 | Clerc et al. |
| 6,494,829 B1 | 12/2002 | New, Jr. et al. |
| 6,507,759 B1 | 1/2003 | Prutchi et al. |
| 6,539,253 B2 | 3/2003 | Thompson et al. |
| 6,575,912 B1 | 6/2003 | Turcott |
| 6,577,901 B2 | 6/2003 | Thompson |
| 6,584,352 B2 | 6/2003 | Combs et al. |
| 6,599,250 B2 | 7/2003 | Webb et al. |
| 6,615,074 B2 | 9/2003 | Mickle et al. |
| 6,631,296 B1 | 10/2003 | Parramon et al. |
| 6,636,769 B2 | 10/2003 | Govari et al. |
| 6,638,231 B2 | 10/2003 | Govari et al. |
| 6,645,143 B2 | 11/2003 | VanTassel et al. |
| 6,645,153 B2 | 11/2003 | Kroll et al. |
| 6,650,944 B2 | 11/2003 | Goedeke et al. |
| 6,652,464 B2 | 11/2003 | Schwartz et al. |
| 6,656,117 B2 | 12/2003 | Jentsch et al. |
| 6,658,300 B2 | 12/2003 | Govari et al. |
| 6,659,959 B2 | 12/2003 | Brockway et al. |
| 6,667,725 B1 | 12/2003 | Simons et al. |
| 6,682,490 B2 | 1/2004 | Roy et al. |
| 6,692,446 B2 | 2/2004 | Hoek |
| 6,699,186 B1 | 3/2004 | Wolinsky et al. |
| 6,728,576 B2 | 4/2004 | Thompson et al. |
| 6,746,404 B2 | 6/2004 | Schwartz |
| 6,749,566 B2 | 6/2004 | Russ |
| 6,766,201 B2 | 7/2004 | Von Arx et al. |
| 6,783,499 B2 | 8/2004 | Schwartz |
| 6,786,905 B2 | 9/2004 | Swanson et al. |
| 6,788,973 B2 | 9/2004 | Davis et al. |
| 6,795,732 B2 | 9/2004 | Stadler et al. |
| 6,796,942 B1 | 9/2004 | Kreiner et al. |
| 6,810,290 B2 | 10/2004 | Lebel et al. |
| 6,813,519 B2 | 11/2004 | Lebel et al. |
| 6,821,249 B2 | 11/2004 | Casscells, III et al. |
| 6,847,844 B2 | 1/2005 | Sun et al. |
| 6,852,084 B1 | 2/2005 | Boesen |
| 6,855,115 B2 * | 2/2005 | Fonseca et al. ............... 600/488 |
| 6,858,006 B2 | 2/2005 | MacCarter et al. |
| 6,878,111 B2 | 4/2005 | Kenknight et al. |
| 6,890,300 B2 | 5/2005 | Lloyd et al. |
| 6,895,265 B2 | 5/2005 | Silver |
| 6,895,281 B1 | 5/2005 | Amundson et al. |
| 6,908,437 B2 | 6/2005 | Bardy |
| 6,915,157 B2 | 7/2005 | Bennett et al. |
| 6,926,670 B2 | 8/2005 | Rich et al. |
| 6,963,771 B2 * | 11/2005 | Scarantino et al. ............ 600/436 |
| 6,968,743 B2 | 11/2005 | Rich et al. |
| 6,970,742 B2 | 11/2005 | Mann et al. |
| 7,418,868 B1 | 9/2008 | Karicherla et al. |
| 2001/0044588 A1 | 11/2001 | Mault |
| 2002/0077553 A1* | 6/2002 | Govari et al. .................. 600/486 |
| 2002/0077556 A1 | 6/2002 | Schwartz |
| 2002/0123777 A1 | 9/2002 | Dolgin et al. |
| 2002/0138009 A1 | 9/2002 | Brockway et al. |
| 2002/0151770 A1 | 10/2002 | Noll et al. |
| 2002/0151816 A1* | 10/2002 | Rich et al. ..................... 600/547 |
| 2002/0183628 A1 | 12/2002 | Reich et al. |
| 2003/0009088 A1 | 1/2003 | Korth et al. |
| 2003/0083719 A1 | 5/2003 | Shankar et al. |
| 2003/0135246 A1 | 7/2003 | Mass et al. |
| 2003/0149459 A1 | 8/2003 | Von Arx et al. |
| 2004/0030581 A1 | 2/2004 | Leven |
| 2004/0044382 A1 | 3/2004 | Ibrahim |
| 2004/0111034 A1 | 6/2004 | Lin et al. |
| 2004/0113790 A1 | 6/2004 | Hamel et al. |
| 2004/0122487 A1 | 6/2004 | Hatlestad et al. |
| 2004/0147982 A1 | 7/2004 | Bardy |
| 2004/0167580 A1 | 8/2004 | Mann et al. |
| 2004/0167587 A1 | 8/2004 | Thompson |
| 2004/0176811 A1 | 9/2004 | Von Arx et al. |
| 2004/0193029 A1 | 9/2004 | Glukhovsky |
| 2004/0193058 A1 | 9/2004 | Montegrande et al. |
| 2004/0215083 A1 | 10/2004 | Shimizu et al. |
| 2004/0215084 A1 | 10/2004 | Shimizu et al. |
| 2004/0215291 A1 | 10/2004 | Van Bentem |
| 2004/0225337 A1 | 11/2004 | Housworth et al. |
| 2004/0254455 A1 | 12/2004 | Iddan |
| 2004/0254483 A1 | 12/2004 | Zdeblick et al. |
| 2005/0004478 A1 | 1/2005 | Fitz |
| 2005/0015014 A1 | 1/2005 | Fonseca et al. |
| 2005/0021109 A1 | 1/2005 | Samsioe |
| 2005/0038345 A1 | 2/2005 | Gorgenberg et al. |
| 2005/0043765 A1 | 2/2005 | Williams et al. |
| 2005/0065592 A1 | 3/2005 | Holzer |
| 2005/0075688 A1 | 4/2005 | Toy et al. |
| 2005/0075689 A1 | 4/2005 | Toy et al. |
| 2005/0075693 A1 | 4/2005 | Toy et al. |
| 2005/0102026 A1 | 5/2005 | Turner et al. |
| 2005/0113647 A1 | 5/2005 | Lee et al. |
| 2005/0113885 A1 | 5/2005 | Haubrich et al. |
| 2005/0113886 A1 | 5/2005 | Fischell et al. |
| 2005/0131494 A1 | 6/2005 | Park et al. |
| 2005/0148883 A1 | 7/2005 | Boesen |
| 2005/0159653 A1 | 7/2005 | Iijima et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187487 A1* | 8/2005 | Azizkhan et al. .............. 600/561 |
| 2007/0032734 A1 | 2/2007 | Najafi et al. |

FOREIGN PATENT DOCUMENTS

| | | |
|---|---|---|
| DE | 4341903 | 6/1995 |
| DE | 102004055220 A1 | 5/2006 |
| EP | 1101440 | 5/2001 |
| EP | 1174079 | 1/2002 |
| EP | 1312302 A2 | 5/2003 |
| WO | WO-9733513 | 9/1997 |
| WO | WO-0016686 | 3/2000 |
| WO | WO-02065894 | 8/2002 |
| WO | WO-2005018444 | 3/2005 |
| WO | WO-2005048835 | 6/2005 |
| WO | WO-2005051189 A2 | 6/2005 |
| WO | WO-2005082243 | 9/2005 |
| WO | WO-2006009467 | 1/2006 |
| WO | WO-2006072776 | 7/2006 |

OTHER PUBLICATIONS

George Akingba, Adrienne Cheng, Angela Shum, Peter Yang, "An Implantable Pressure Sensor for Aneurysmal Disease", published no later than Sep. 30, 2003.

M. Gaweenda, J. Heckenkamp, S. Winter, G. Jaschke, J. Brunkwall, "Pressure is Transmitted Through PTFE and Dacron Grafts Leading to Aneurysm Sac Pressure Following Endoluminal Grafting of AAA—An In Vitro Study," Vascular Centre, University of Cologne, Germany, , published no later than Sep. 30, 2003.

H.E. Haynes and A.L. Witchey, "Medical Electronics: The Pill That "Talks"," RCA Engineer, pp. 52-54, vol. 5, No. 5, Feb.-Mar. 1960.

John T. Farrar, Carl Berkley, Vladimmir K. Zworykin, "Telemetering of Intraenteric Pressure in Man by an Externally Energized Wireless Capsule," Science, New Series Issue 3416, Jun. 1960, p. 1814, vol. 131.

Thomas B. Fryer, Harold Sandler, William Freund, Ernest P. McCutcheon, and Edwin L. Carlson, "A Multichannel Implantable Telemetry System for Flow, Pressure, and ECG Measurements," Journal of Applied Physiology, vol. 39, No. 2, Aug. 1975, pp. 318-326.

Tayfun Akin, Babak Ziaie, and Khalil Najafi, "RF Telemetry Powering and Control of Hermetically Sealed Integrated Sensors and Actuators," Digest, Solid-State Sensors and Actuators Workshop, Hilton Head, SC Jun. 1990, pp. 145-148.

VDI/VDE-IT 1994, Micro System Technology Implantable Telemetrically Endo Systems (ITES), 1995-1997 publication.

David M. Steinhaus, Robert Lemery, Dennis R. Bresnahan, Jr., Larry Handlin, Tom Bennett, Alan Moore, Debbie Cardinal, Laura Foley, Richard Levine, "Initial Experience With an Implantable Hemodynamic Monitor," American Heart Association Circulation, 1996, vol. 93, pp. 745-752.

A. Ohlsson, T. Bennett, F. Ottenhoff, C. Bitkover, B. Kjellstrom, R. Nordlander, H. Astrom and L. Ryden, "Long-Term Recording of Cardiac Output Via an Implantable Haemodynamic Monitoring Device," European Heart Journal, vol. 17, Dec. 1996, pp. 1902-1910.

T. Chuter, K. Ivancev, M. Malina, T. Resch, J. Brunkwall, B. Lindblad and B. Risberg, Endovascular and Surgical Techniques, "Aneurysm Pressure following Endovascular Exclusion," Eur J Vasc Endovasc Surg., vol. 13, pp. 85-87, 1997.

G.W.H. Schurink, N.J.M. Aarts, J. Wilde, J.M. Van Baalen, T.A.M. Chuter, L.J. Schultze Kool, and J.H. Vanbockel, "Endoleakage After Stent-Graft Treatment of Abdominal Aneurysm: Implications on Pressure and Imaging—an In Vitro Study," Journal of Vascular Surgery, vol. 28, No. 2, pp. 234-241, Aug. 1998.

Gareth D. Treharne, Ian M. Loftus, Matthew M. Thompson, Nicola Lennard, Julia Smith, Guy Fishwick, and Peter R.F. Bell, "Quality Control During Endovascular Aneurysm Repair: Monitoring Aneurysmal Sac Pressure and Superficial Femoral Artery Flow Velocity," Journal of Endovascular Surgery, 1999, vol. 6 pp. 239-245.

P.L. Harris and S. Dimitri, "Predicting Failure of Endovascular Aneurysm Repair," Eur J Vasc Endovasc Surg., vol. 17, pp. 1-2, 1999.

V. Bodecker, C. Bodecker-Kuhnert, S. Meyer, "The Mesograph: A New Technological Solution for Continuous IOP Monitoring", Proceedings of the World Microtechnologies Congress MICRO.tec 2000, vol. 2, Hanover, Germany, S. 437-440, 2000.

G.W.H. Schurink, N.J.M. Aarts, J.M. Van Baalen, L.J. Schultze Kool and J.H. VanBockel, "Experimental Study of the Influence of Endoleak Size on Pressure in the Aneurysm Sac and the Consequences of Thrombosis," British Journal of Surgery 2000, pp. 87, 71-78.

Jiang Zhe, K.R. Farmer and Vijay Modi, "A MEMS Device for Measurement of Skin Friction with Capacitive Sensing," "Microelectromechanical Systems Conference, 2001", Berkeley, CA, pp. 4-7.

Richard A. Baum, Jeffrey P. Carpenter, Constantin Cope, Michael A. Golden, Omaida C. Velazquez, David G. Neschis, Marc E. Mitchell, Clyde F. Barker, and Ronald M. Fairman, "Aneurysm Sac Pressure Measurements After Endovascular Repair of Abdominal Aortic Aneurysms," Journal of Vascular Surgery, Jan. 2001, vol. 33, No. 1, pp. 32-41.

Mark L. Manwaring, Veljko D. Malbasa, Kim L. Manwaring, "Remote Monitoring of Intracranial Pressure," Annals of the Academy of Studencia, Apr. 2001, pp. 77-80, 2001.

A. Ohlsson, S.H. Kubo, D. Steinhaus, D.T. Connelly, S. Adler, C. Bitkover, R. Nordlander, L. Ryden and T. Bennett, "Continuous Ambulatory Monitoring of Absolute Right Ventricular Pressure and Mixed Venous Oxygen Saturation in Patients with Heart Failure Using an Implantable Haemodynamic Monitor," European Heart Journal, vol. 22, Issue 11, Jun. 2001, pp. 942-954.

Juan Carlos Parodi, Ramon Berguer, Luis Mariano Ferreira, Ricardo La Mura, and Mark L. Shermerhorn, "Intra-aneurysmal Pressure After Incomplete Endovascular Exclusion," Journal of Vascular Surgery, Nov. 2001, vol. 34, No. 5, pp. 909-914.

M. Gawenda, J. Heckenkamp, M. Zaehringer and J. Brunkwall, "Intra-aneurysm Sac Pressure—The Holy Grail of Endoluminal Grafting of AAA," Eur J Vas Endovasc Surg 24, 139-145, 2002.

Kirkwood F. Adams, Jr., "Guiding Heart Failure Car by Invasive Hemodynamic Measurements: Possible or Useful?," Journal of Cardiac Failure, vol. 8, No. 2, 2002, pp. 71-73.

Anthony Magalski, Philip Adamson, Frederick Gadler, Michael Boehm, David Steinhaus, Dwight Reynolds, Kathryn Vlach, RN, Cecilia Linde, Bodo Cremers, Brandon Sparks, Tom Bennett, "Continuous Ambulatory Right Heart Pressure Measurements With an Implantable Hemodynamic Monitor: A Multicenter, 12-Month Follow-up Study of Patients With Chronic Heart Failure," Journal of Cardiac Failure, vol. 8, No. 2, 2002, pp. 63-70.

Andrew DeHennis and Kensall D. Wise, "A Passive-Telemetry-Based Pressure Sensing System," Proc. Solid State Sensors and Actuators Workshop, Hilton Head, SC 2002, pp. 165-168.

Andrew DeHennis and Kensall D. Wise, "A Double-Sided Single-Chip Wireless Pressure Sensor," Digest IEEE Conference on MicroElectroMechanical Systems, Las Vegas, pp. 252-255, Jan. 2002.

F. Braunschweig, C. Linde, M.J. Eriksson, C. Hofman-Bang and L. Ryden, "Continuous Haemodynamic Monitoring During Withdrawal of Diuretics in Patients with Congestive Heart Failure," European Heart Journal, vol. 23, Issue 1, Jan. 2002, pp. 59-69.

C. Shawn Skillern, Scott L. Stevens, K. Todd Piercy, Robert L. Donnell, Michael B. Freeman, and Mitchell H. Goldman, "Endotension in an Experimental Aneurysm Model," Journal of Vascular Surgery, Oct. 2002, vol. 36, No. 4, pp. 814-817.

John P. Boehmer, "Device Therapy for Heart Failure," The American Journal of Cardiology, vol. 91(6A), Mar. 20, 2003, pp. 53D-59D.

S.R. Vallabhaneni, J. Brennan, G. Gilling-Smith, D. Gould, T. How, R. McWilliams, P.L. Harris, "Aortic Side Branch Perfusion Alone Does not Account for High Intra-Sac Pressure After Endovascular Repair (EVAR) in the Absense of Graft-Related Endoleak", European Journal of Vascular and Endovascular Surgery, vol. 25, Issue 4, Apr. 2003, pp. 354-359.

Bjorn Sonesson, Nuno Dias, Martin Malina, Perake Olofsson, Dennis Griffin, Bengt Lindblad, and Krassi Ivancev, "Intra-Aneurysm Pressure Measurements in Successfully Excluded Abdominal Aortic Aneurysm After Endovascular Repair," Journal of Vascular Surgery, Apr. 2003, pp. 733-738.

Ralph Shabetai, "Monitoring Heart Failure Hemodynamics With an Implanted Device: Its Potential to Improve Outcome," Journal of the American College of Cardiology, vol. 41, No. 4, 2003, pp. 572-573.

A. Ohlsson, D. Steinhaus, B. Kjellstrom, L. Ryden, T. Bennett, "Central Hemodynamic Responses During Serial Exercise Tests in Heart Failure Patients Using Implantable Hemodynamic Monitors," The European Journal of Heart Failure, vol. 5, 2003, pp. 253-259.

Philip B. Adamson, Anthony Magalski, Frieder Braunschweig, Michael Bohm, Dwight Reynolds, David Steinhaus, Allyson Lyby, Ceilia Linde, Lars Ryden, Bodo Cremers, Teri Takle, Tom Bennett, "Ongoing Right Ventricular Hemodynamics in Heart Failure," Journal of the American College of Cardiology, vol. 41, No. 4, 2003, pp. 565-571.

Kenton R. Kaufman, Tom Wavering, Duane Morrow, Jennifer Davis, Richard L. Lieber, "Performance charactericsts of a Pressure Microsensor," Journal of Biomechanics, vol. 36, 2003, pp. 283-287.

Torsten Eggers and Matthias Wenzel, "Implantable Telemetric Pressure Measurement," Med. Device Technol., May 2004, 15(4), pp. 25-27.

Philip B. Adamson, Andrew L. SmithWilliam T. Abrahamkaren J. Kleckner, Robert W. Stadler, Alex Shih, Melissa M. Rohodes, "Continuous Autonomic Assessment in Patients With Symptomatic Heart Failure," American Heart Association Journals, Circulation, Oct. 19, 2004, pp. 2389-2394.

Tom Bennett, Barbro Kjellstrom, Robert Taepke, and Lars Ryden, "Development of Implantable Devices for Continuous Ambulatory Monitoring of Central Hemodynamic Values in Heart Failure Patients," PACE, vol. 28, Jun. 2005, pp. 573-584.

David Steinhaus, Dwight W. Reynolds, Frederick Gadler, G. Neal Kay, Mike F. Hess, and Tom Bennett, "Implant Experience with an Implantable Hemodynamic Monitor for the Management of Symptomatic Heart Failure," PACE, vol. 28, Aug. 2005, pp. 747-753.

Transoma Medical, "LVP-1000 Left Ventricular Pressure Telemetry," <http://www.datasci.com/research/lvp1000.html>, accessed Oct. 27, 2005.

Frieder Braunschweig, Barbro Kjellstrom, Mats Soderhall, Naomi Clyne, Cecilia Linde, "Dynamic Changes in Right Ventricular Pressures During Haemodialysis Recorded with an Implantable Haemodynaamic Monitor," Nephrology Dialysis Transplantation, 2006, vol. 21, pp. 176-183.

International Search Report and Written Opinion for PCT/2006/060798.

International Search Report and Written Opinion for PCT/2006/060800.

* cited by examiner

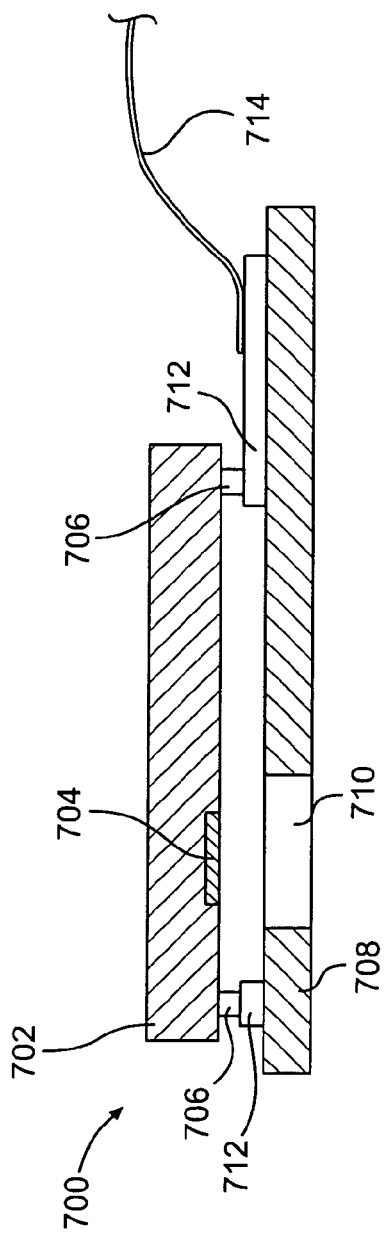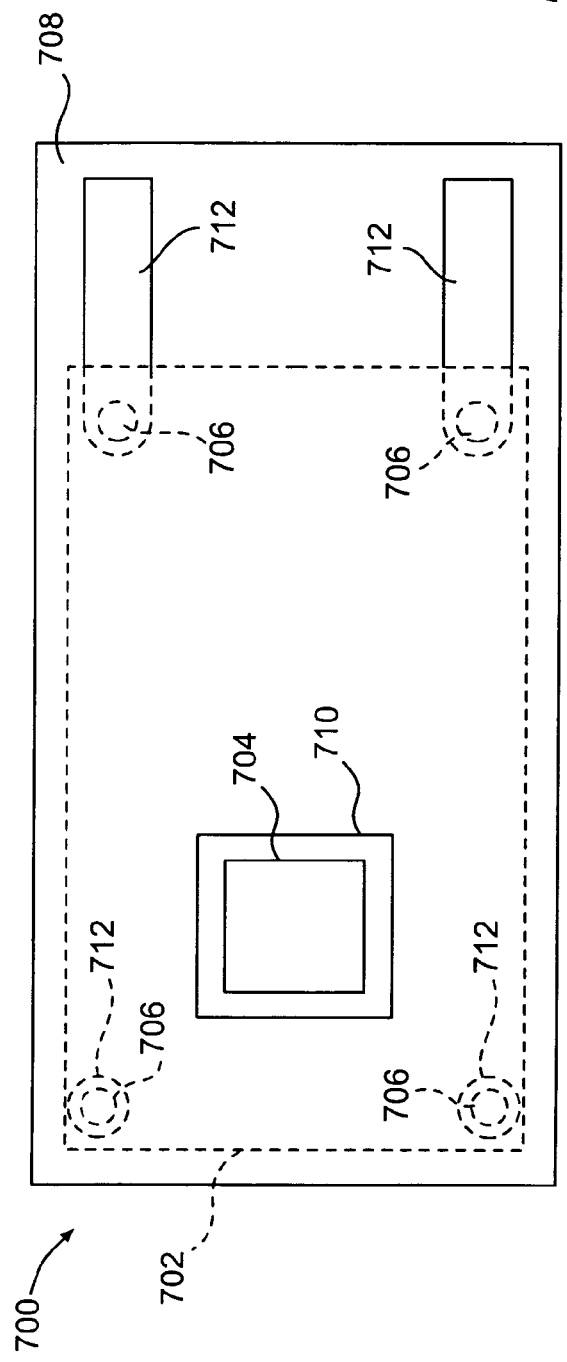

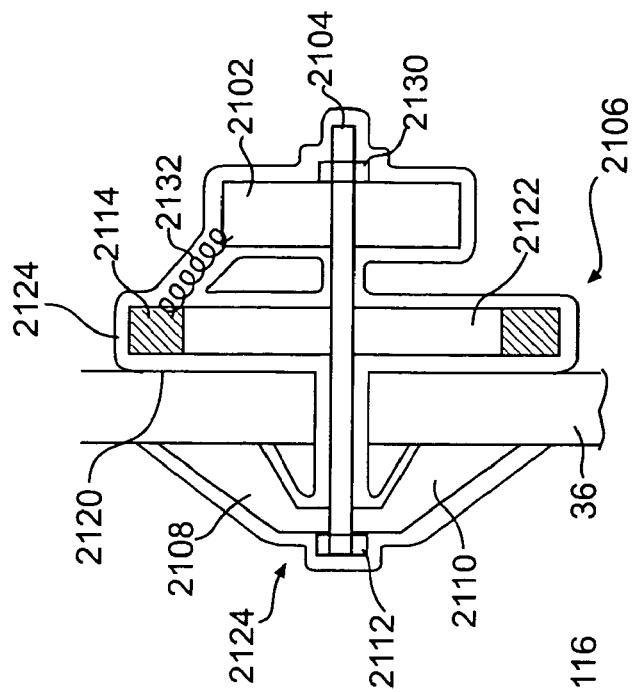
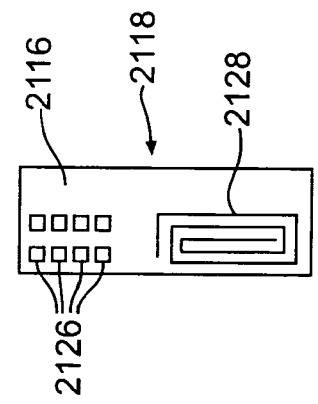
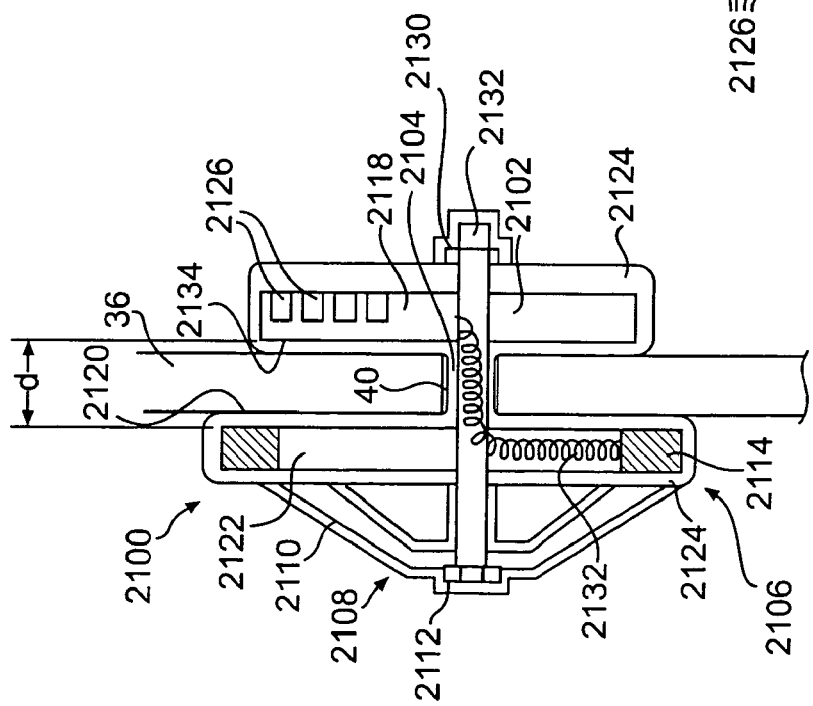

ANCHORED IMPLANTABLE PRESSURE MONITOR

CROSS-REFERENCE TO RELATED APPLICATION

This application is a continuation of U.S. application Ser. No. 11/515,915, filed Sep. 6, 2006, hereby incorporated herein by reference, which incorporates by reference U.S. provisional application Ser. No. 60/738,980, filed Nov. 23, 2005, and U.S. provisional application Ser. No. 60/773,344, filed Feb. 15, 2006. This application also hereby incorporates herein by reference U.S. application Ser. No. 11/452,920, filed Jun. 15, 2006.

FIELD

The invention is directed generally to a method and apparatus and for sensing a characteristic of a patient, such as blood pressure and/or temperature, and more particularly to methods and devices particularly adapted for telemetric measurement of blood pressure by a device implanted via a catheter within the cardiovascular system and particularly within the heart.

BACKGROUND

The National Institute of Health (NIH) has concluded that heart failure constitutes "a new epidemic" in the USA. Heart failure, a chronic, progressive and incurable disease, affects over 20 million people worldwide. In the US alone, some 5 million people have been diagnosed with heart failure. Heart failure is estimated to cost the US economy today more than $40 billion annually.

Intracardiac pressure management is an important aspect of heart failure treatment. For example, a rise of the intracardiac pressure, such as in the left atrium is an important early indication of disease progression and the first opportunity for therapeutic intervention. Current blood pressure-measuring methods only can be applied in the coronary care unit (CCU) or the intensive care unit (ICU) and provide no more than an occasional snapshot of intracardiac pressure when the patient is already in a very critical situation. The limitations on current intracardiac pressure measurement methods are a serious impediment to early and optimal treatment. Current treatment methods require hospitalization and may be extremely costly (on average, over $16,000 per patient admittance). The ability to monitor patients and intervene outside of the hospital setting would greatly reduce the number of hospitalizations and extend the lives of those affected by the diagnosis.

Various sensors and devices have been used or proposed for the measurement and analysis of the blood pressure and/or temperature of a patient with mixed success. The currently contemplated sensors have certain disadvantages. For example, the telemetric sensor described in U.S. Pat. No. 6,855,115 can be implanted in the heart by a catheter. Moreover, the sensor, which is rolled up during the implantation procedure, must be made of a flexible material of a specific configuration so that any change of the blood pressure inside the heart effectuates a change in the distance of the sensor height, i.e., the distance between the two capacitor plates used in the sensor. This flexible sensor is folded for delivery via a catheter and then unfolded at the place of implantation. However, a disadvantage of such a configuration is its required flexibility as constant and precise acquisition of measurement data may not be possible when the sensor is placed on or close to the cardiac muscle, and therefore is exposed to the cardiac motions, which may influence correct pressure readings. In addition, the flexible material of a sensor made in accordance with U.S. Pat. No. 6,855,115 may deform due to exposure to constantly streaming liquids, especially a turbulent blood stream likely encountered inside the heart. As a consequence, the capacitance of the capacitor may be changed and measurement values may deteriorate and/or deviate from the true value. Another disadvantage of this type of sensor is due to its use of a pressure-dependent LC-oscillator. The resonant frequency of this oscillator can be analyzed telemetrically. In principle, this kind of device can be applied to measure the pressure that affects the measurement capacitor. Thus, any damage to the material can affect the pressure measurements obtained. Further, as the sensor is influenced by the surrounding media of the sensor, a corruption of measurement values may occur. In addition, there is no circuitry in this type of sensor to digitize the pressure measurement values acquired. Using analog signals may result in external interference during the acquisition and transmission of data, which causes inaccuracies in readings.

Another exemplary implantable device, described in U.S. Pat. No. 6,409,674, uses a catheter filled with a pressure transmitting fluid or gel-like material. The catheter transmits pressure to a pressure transducer within a housing. The sensed pressure is then telemetrically transmitted to an external reader. However, such a device requires a housing for the electronic signal processing circuitry, which results in a larger and heavier sensor structure that can cause strain on the heart when implanted into a heart wall. Moreover, the catheter and housing configuration creates a more complicated, mechanical structure that may be at increased risk for mechanical failure, and therefore is not suitable for long term implantation.

Another device, described in U.S. Pat. No. 6,970,742, has a pressure sensor placed within the heart. A signal from the pressure sensor is transmitted to a housing outside the heart which contains the electronic processing circuits. The signal is processed by the electronic processing circuits, such as converting the signals from analog to digital, and then telemetrically transmitted to an external reader. However, housing the electronic processing circuitry requires additional components and a relatively larger implanted device. Moreover, because digitization of the signal does not occur until outside of the heart, there is a risk of interference in the wire connecting the sensor and the electronic processing circuitry, as analog interference may result from external sources.

Small pressure sensor chips including the electronic processing circuits have been used in other applications. For example, integrated chips having pressure sensors have been used for pressure measurement in optical and cranial applications. These sensors are compact and have fewer mechanical components. Examples of such pressure sensor chips are described in EP 1 312 302 A2 and German Pat. application DE 10 2004 055 220.7, of which the inventors of the present invention were involved. However, these integrated chips are used in a relatively stable environment, with little movement in the fluids of the eye or brain. Nor are these pressure sensors subject to the cyclical, dynamic movements found in the heart. Such movement may harm connections, such as connections between wires and the pressure sensing chip. Thus, the use of such pressure sensor chips is not suited for the environment of the heart, where there is cyclical and dynamic movement, and where there is continuous and turbulent fluid movement around the pressure sensor.

Conventional techniques to provide stability and support to such known pressure sensing chips to enable their use as a cardiovascular pressure sensors would not likely succeed.

Directly attaching a wire to a pressure sensing chip may have a negative impact on the functionality of the chip. For example, when soldering is used for the connection, the heat may damage the chip. One known method of avoiding that problem is to adhere a substrate to the back of the pressure sensing chip, solder the wire to a bond tack on that substrate, and then connect the wire to the chip. However, such substrates have different coefficients of thermal expansion than the chip. Thus, as the temperature changes, the substrate expands and contracts at a different rate then the pressure sensor chip, thereby causing stress and strain on the pressure sensing chip and increasing the risk of damage and/or inoperability.

Other known pressure sensors require a cable connection between the pressure sensor inside the heart and the external body monitoring device. However, such a cable clearly requires an entry into the body. An entry may be inconvenient and require the implantation of both the device and the entry, as well as increase the risk of infection for the patient.

Thus, there is a need for intra-cardiac pressure sensors that are more reliable and accurate, and which cause less irritation when implanted in the heart and are more compatible with the dynamic conditions encountered in a moving heart. Also, a need exists for such a sensor to be used at other locations within the cardiovascular system with little or no modifications.

Further, there is a need for a delivery mechanism for the sensor that can deliver and securely anchor a substantially rigid, sensor chip of invention in any part of the heart or other parts of cardiovascular system, such as the great vessels.

SUMMARY

The invention meets the above needs and avoids the disadvantages and drawbacks of the prior art by providing a substantially rigid, chip-based telemetric sensor and system in which an extremely small and lightweight chip, including at least one pressure sensor and all necessary electrical circuitry, may be placed in the heart or other portion of the cardiovascular system via a catheter or other minimally-invasive procedure, to monitor blood pressure and/or temperature.

In this manner, pressure signals may be digitized at or near the sensing location in the heart or other location in the cardiovascular system and data may be telemetrically directed to the place of data acquisition to reduce or eliminate data transmission interference from external sources.

In particular, the chip may be a substantially rigid structure that provides improved durability, long term stability, and long term accuracy, and resistance to damage or a change in membrane characteristics from the blood flow due to turbulences and the like within the bloodstream. For example, the chip may be an application specific integrated chip (ASIC) containing all the necessary sensing elements and digital signal processing electronics. The ASIC preferably is very small and lightweight to avoid undue stress on the heart and is orientated within the body in a position to minimize turbulent flow and reactionary forces. The ASIC may be used with an antenna in the form of a coil created with very small dimensions. This minimal configuration of ASIC and coil may reduce and/or eliminate mechanical tensions effecting the connection between ASIC and a coil.

The ASIC and coil may be encapsulated within a seamless biocompatible and flexible sheathing, such as silicone or similar material, to form an integrated sensor unit. The seamless sheathing may maintain the integrity of the sensor by reducing or eliminating the exposure of the sensor to body fluids, such as blood. It may also be shaped and/or orientated to reduce turbulent flow.

A liquid or gel may be placed between the pressure sensing elements, such as capacitive membrane sensors of the sensor and the sheathing, to reduce or eliminate the effects of endothelialization on the surface of the sensor. The liquid or gel allows for integrating the pressure across the entire area of pressure sensing portion of the sensor to minimize the effects of localized plaque or endothelialization. The sheathing material itself may act as a pressure transmitting material instead of the liquid or gel. Of course, heparin and other preventative coatings known in the art also may be used to prevent or reduce endothelialization.

To protect the ASIC and particularly the membrane sensor elements from damage during the implantation procedure, such as strain and stress due to bending of the tip of the catheter during insertion and/or unfolding of the antenna, or from damage due to handling, e.g., as a consequence of contact with a surgical instrument during implantation and/or during use, the sensor design may have a unique geometry. For example, the ASIC may be connected to a substantially rigid substrate in a spaced apart relationship from the ASIC such that the substrate is opposite the pressure sensing elements of the sensor chip, with an aperture in the substrate providing access to the pressure elements to expose them to fluid pressure to be sensed. A silicone or other similar flexible material may be disposed between the ASIC and the substrate. Moreover, a pressure transmitting material may be placed within the gap between the ASIC and the rigid substrate so that pressure from the blood can be transmitted to the pressure elements via the material.

The ASIC may incorporate a robust system to compensate for drift due to the age and use of the sensor. For example, the ASIC may include inactive pressure sensing elements that determine the change in the measurement in the sensor due to age and usage, and may account for this change when active pressure sensing elements determine the pressure.

The ASIC is powered by induction from a wireless signal from an external reader, thereby avoiding the need for an internal power source. Use of a transponder power supply at the external reader allows for a substantially rigid sensor chip with a longer life. The external reader provides power to the substantially rigid sensor and receives pressure and temperature information from the substantially rigid sensor. The external reader stores and displays measurement and parameter data, calculates certain values. The external reader stores and displays measurement and parameter data, and may transmit the data to a computer or other device for further processing. The external reader may have a separate antenna coil to facilitate prolonged periods on a patient's body. The external reader may store one or more calibration curves for different sensors. The external reader may also have a pressure sensor to measure the surrounding air pressure and to calculate the difference between the absolute pressure within the heart and the absolute pressure of the air surrounding the patient.

The ASIC, antenna coil and an anchor may be delivered and implanted into the cardiovascular system of a patient via a catheter. The ASIC, coil and anchor are sized to fit within a lumen of a catheter. The anchor is expandable from the catheter to mount the ASIC and coil within the cardiovascular system, such as within the heart or the great vessels.

The telemetric pressure and/or temperature sensor of the invention may be used for continuous or on demand sensing. A specific identification number may be transmitted with each single measurement or measurement cycle. In this way, a continuous measurement value and sensor identification, and therefore the measurement value and the identity of the patient, is provided. The identification number may allow a single external reader to receive data from multiple sensors and systems and to assign them to the correct calibration curve for that sensor system and the patient.

The invention may be implemented in a number of ways. According to one aspect of the invention, an intra-cardiac pressure measuring system for measuring blood pressure inside the cardiovascular system of a patient includes an antenna and an integrated chip including a first substantially rigid substrate, at least one pressure sensor disposed within the substrate to generate signals indicative of a sensed pressure, and electronic signal processing components to process the signals generated by the at least one pressure sensor. The electronic signal processing components are operatively connected to the antenna, and the integrated chip is powered by a signal received at the antenna. An anchor structure mounts the integrated chip to a wall in the cardiovascular system such that the at least one pressure sensor is exposed to blood. A remote receiver is provided such that the integrated chip is operative to send digital signals indicative of the pressure sensed in the heart telemetrically via the antenna to the remote receiver. The antenna, the integrated chip and the anchor structure are sized to fit within a delivery catheter for implantation in the cardiovascular system.

The system may measure blood pressure within at least one heart chamber or one of the great vessels. The at least one pressure sensor may include capacitive-based pressure sensitive membranes housed within the substrate. The at least one pressure sensor may generate an analog signal in response to a sensed pressure and the electronic signal processing components may include at least one analog to digital (A/D) converter to digitize within the heart the analog signals from the at least one pressure sensor. The system integrated chip may weigh less than about one gram, have a surface area on one side of less than or equal to about 25 mm$^2$ and have a thickness of less than about 1 mm.

The antenna, the chip, and the anchor structure may be encapsulated in a seamless, one-piece biocompatible sheathing. A pressure transferring medium may be interposed between the biocompatible sheathing and the at least one pressure sensor. The biocompatible sheathing may act as a pressure transferring medium to said at least one pressure sensor. The sheathing may be shaped to minimize turbulence in blood flow within the heart.

The integrated chip may further include a unique digital identification, wherein the unique digital identification is sent telemetrically to the receiver. The receiver may obtain calibration information associated with the integrated chip based on the unique digital identification. The receiver may include a stored parameter and produce an alert based on the signals indicative of the pressure sensed in the heart and of the stored parameter.

The integrated chip may include a first integrated chip and a second integrated chip, wherein the first integrated chip and the second integrated chip are physically and/or operatively connected, e.g., via strain relief connection(s). The first integrated chip may include the at least one pressure sensor and at least one analog to digital (A/D) converter, and the second integrated chip is operably connected to the antenna. The first integrated chip may be located in a different chamber of the heart than the second integrated chip.

The at least one pressure sensor may include a plurality of pressure sensors including at least one active sensor responsive to changes in pressure within the heart and at least one passive sensor that is isolated from the changes in pressure within the heart, wherein the electronic signal processing components may provide a signal based at least in part on a signal from the at least one active pressure sensor and a signal from the at least one passive pressure sensor. The pressure signals may be the result of offsetting the signal from the at least one active pressure sensor with the signal from the at least one passive pressure sensor. The structure of the active pressure sensor may be substantially the same as a structure of the passive pressure sensor. The plurality of pressure sensors may include capacitive pressure sensors each having a flexible movable membrane. The passive pressure sensor signal may be responsive to a change in position of the membrane of the passive pressure sensor and the change of position of the membrane of the passive pressure sensor may be due to a drift effect comprising a sag of the membrane. The change of position of the membrane of the active pressure sensor may be due to a change in pressure within the heart or a drift effect comprising a sag of the membrane.

The substantially rigid sensor may include a surface that cooperates with the anchor structure to mount the antenna and the substantially rigid sensor chip within the heart. The anchor structure may mount the antenna and the substantially rigid sensor chip to the cardiac septum. The antenna may be mounted to one side of the cardiac septum and the substantially rigid sensor may be mounted to the other side of the septum. Alternatively, the antenna and the substantially rigid sensor may be mounted on the same side of the septum. The antenna may include a first surface adjacent to the cardiac septum and a second surface adjacent to at least a portion of the anchor structure. The anchor structure may include a resilient member that enables the anchor structure to expand from a compressed position shape that fits within a lumen of a delivery catheter to an expanded position. The resilient member may include wire loops. The antenna may be flexible and foldable to fit within the lumen of a delivery catheter. The substantially rigid sensor may further include a temperature sensor.

The pressure measuring system may be delivered by a catheter. The catheter includes a catheter lumen having a hollow portion and a first opening, and a system guide operative to laterally move the pressure measuring system within the hollow portion and out of the first opening in said catheter lumen. The integrated chip may have a conic shape operative to pierce a wall or organ of the patient.

According to another aspect of the invention a method of sensing blood pressure within the cardiovascular system of a subject includes the steps of: implanting within the subject a substantially rigid, integrated chip minimally-invasively using at least one catheter, the integrated chip including a substantially rigid substrate and at least one capacitive-based pressure sensor disposed within the substrate in a position to sense blood pressure within the cardiovascular system; powering on the integrated chip telemetrically by activating a power source located outside the subject; obtaining one or more analog signals from the at least one pressure sensor indicative of the pressure at the position in the cardiovascular system; and converting the analog signals to digital signals at or directly adjacent to the position in the cardiovascular system where the sensing occurs.

The implanting step may include implanting an ASIC having a capacitive-based pressure sensor in the heart or in one of the great vessels. The implanting step may also include the steps of delivering the capacitive-based pressure sensor at the position in the cardiovascular system, and mounting the capacitive-based pressure sensor at the position with an anchor structure. The implanting step may further include the steps of delivering the anchor structure at a position to mount the capacitive-based pressure sensor in the cardiovascular system, and expanding at least a portion of the anchor structure. The method may also include the steps of implanting within the subject using a catheter a foldable antenna operatively connected to the integrated chip. The method may further include the step of calculating a waveform of a heart beat based on the sensed blood pressure.

According to another aspect of the invention, an integrated chip for intra-cardiac blood pressure measurement inside a patient includes a first substantially rigid substrate, at least one pressure sensor disposed within the substrate to generate signals indicative of a sensed pressure, and electronic signal processing components to process the signals generated by the at least one pressure sensor, the electronic signal processing components being operatively connected to an antenna, and the integrated chip being powered by a signal received at the antenna. The integrated chip is operative to send digital signals indicative of the pressure sensed in the patient telemetrically via an antenna to a remote receiver and the integrated chip is sized to fit within a delivery catheter for implantation.

The at least one pressure sensor may generate analog signals and the electronic signal processing components may include at least one analog to digital (A/D) converter to digitize within the patient at location where the chip is implanted the analog signals from the at least one pressure sensor. The integrated chip may weigh less than about one gram, have a surface area on one side of less than or equal to about 25 mm$^2$ and have a thickness of less than about 1 mm. The substantially rigid integrated circuit may not be foldable. The integrated chip may further include an expandable antenna operatively connected to the electronic signal processing components, where the antenna may have a compressed position for delivery via the catheter and an expanded position for use after implantation.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings:

FIGS. 7 and 8 schematically illustrate a cross-sectional and top plan view, respectively, of one embodiment of an implantable sensor chip of the invention including a substantially rigid ASIC connected at two ends to a substantially rigid substrate having a cut out;

FIG. 21 schematically illustrates an embodiment of an implantable telemetric measuring device of the invention that is particularly adapted for implantation via catheterization in which the sensor chip and antenna are located on opposite sides of the septum;

FIG. 22 schematically illustrates another embodiment of a telemetric measuring device of the invention that may be implanted via catheterization in which the sensor chip and the antenna are located on the same side of the septum with the heart chamber to be monitored;

FIG. 23 schematically illustrates another embodiment of a substantially rigid sensor chip having an internal data transmission coil that may be used in the telemetric measuring devices of FIGS. 21 and 22;

DETAILED DESCRIPTION

Figure 2:
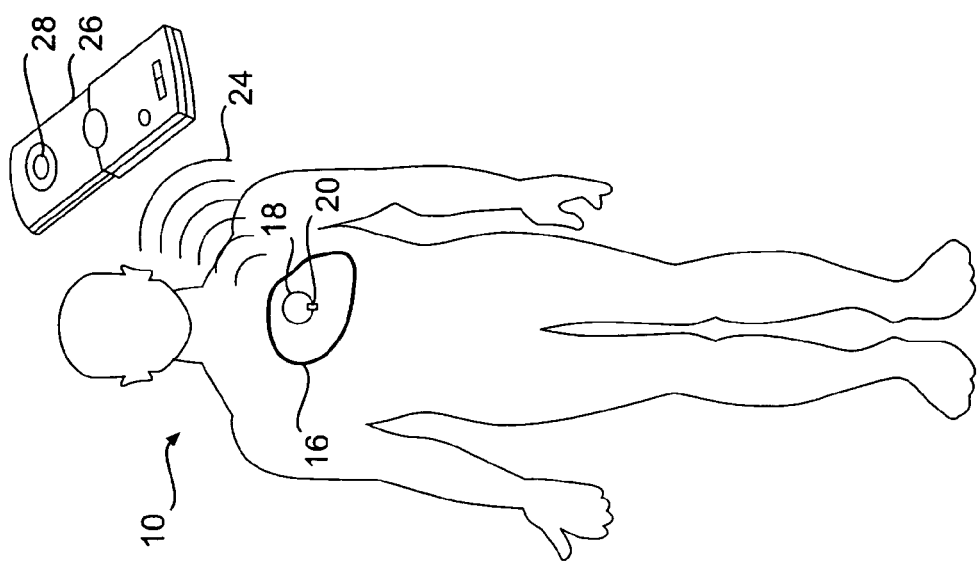
FIG. 2 schematically illustrates another embodiment of an implantable telemetric measuring device and reader constructed according to principles of the invention providing for on-demand intra-cardiac pressure monitor monitoring.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Figure 1:
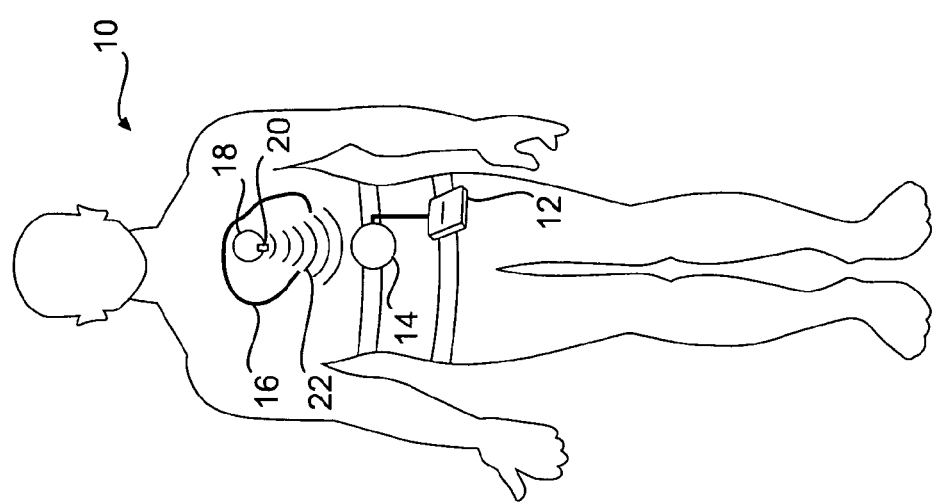
FIG. 1 schematically illustrates an embodiment of an implantable telemetric measuring device and reader constructed according to principles of the invention providing for continuous or regular intra-cardiac pressure monitoring.

FIG. 1 schematically illustrates an embodiment of an implantable telemetric measuring device and reader constructed according to principles of the invention providing for continuous or regular intra-cardiac pressure monitoring. A coil or antenna 14 connected with an external reader 12 generates a radio frequency (RF) field in a manner known in the art. The coil 14 and external reader 12 may be fixed to individual belts that wrap around the patient and connect to each other via a standard cable. The RF field induces a current in a coil 18 connected to a substantially rigid sensor chip 20, such as described herein, implanted within the heart 16 of the patient 10, such as the septum or the wall of the left atrium, to sense pressure in the left atrium. The sensor chip 20 may consist of an application specific integrated circuit (ASIC) such as described herein, having power conditioning circuitry that detects when adequate power is being delivered and switches on sensing, analog-to-digital, and data processing circuits. The data processing circuitry sends the sensor data to the ASIC transmitter, which uses the coil 18 as an antenna. The coil 18 telemetrically transmits, via signal 22, the data to the antenna 14 of the external reader 12. The external reader 12 may provide secure reception and storage of pressure and temperature values, compare the pressure reading of the implanted device 20 to ambient pressure via an internal sensor in the reader, and deliver the intracardiac data to other devices, such as computers, personal digital assistants (PDAs), cell phones, etc., via standard protocols.

In this embodiment, the external reader 12 may obtain data from the sensor chip 20 at continuous or regular intervals. By way of example, the external reader 12 may continuously generate an RF signal to activate the sensor chip 20 to obtain pressure and/or temperature readings (in order to describe even the waveform of the blood pressure, if desired by the doctor, the sensor chip should take up to 100 or more measurements per second). Alternatively, the external reader 12 may generate an RF signal at regular intervals (e.g., every half hour, once ever four hours, once a day) to activate the implanted rigid sensor chip 20 to obtain pressure and/or temperature readings.

FIG. 2 schematically illustrates another embodiment of an implantable telemetric measuring device and reader, which may operate similarly to the FIG. 1 embodiment but provides for on demand intra-cardiac pressure monitoring according to principles of the invention. In this embodiment, a coil 28 in a hand-held reader 26 generates an RF field that induces a current in the coil 18 of the substantially rigid sensor chip 20 implanted within the heart 16 of the patient 10, as in the FIG. 1 embodiment. As described above, sensor chip 20 may include an ASIC that operates similarly to the FIG. 1 embodiment. Thus, power conditioning circuitry in the sensor chip 20 detects when adequate power is being delivered, and turns on the sensing, analog-to-digital, and data processing circuits. The data processing circuitry sends the sensor data to the ASIC transmitter, which uses the coil 18 as an antenna. The coil 18 transmits, via signal 24, the data to the antenna 28 of the hand-held reader 26. The hand-held reader 26 may be extendable to expose the antenna 28 and provides reception and storage of pressure and temperature values, and compares the implant's pressure reading to ambient pressure via an internal sensor in the readout device. The hand-held device 26 may deliver the intracardiac data to other devices, such as computers, PDAs, cell phones, etc., via standard protocols.

In this embodiment, the reader unit 26 may obtain data from the implanted sensor chip 20 on demand. By way of example, a user may activate and cause the reader unit 20 to generate an RF signal by extending the top portion containing the antenna from the bottom portion of the reader unit housing to activate the implanted rigid sensor chip 20 to obtain pressure and/or temperature readings.

Figure 3:
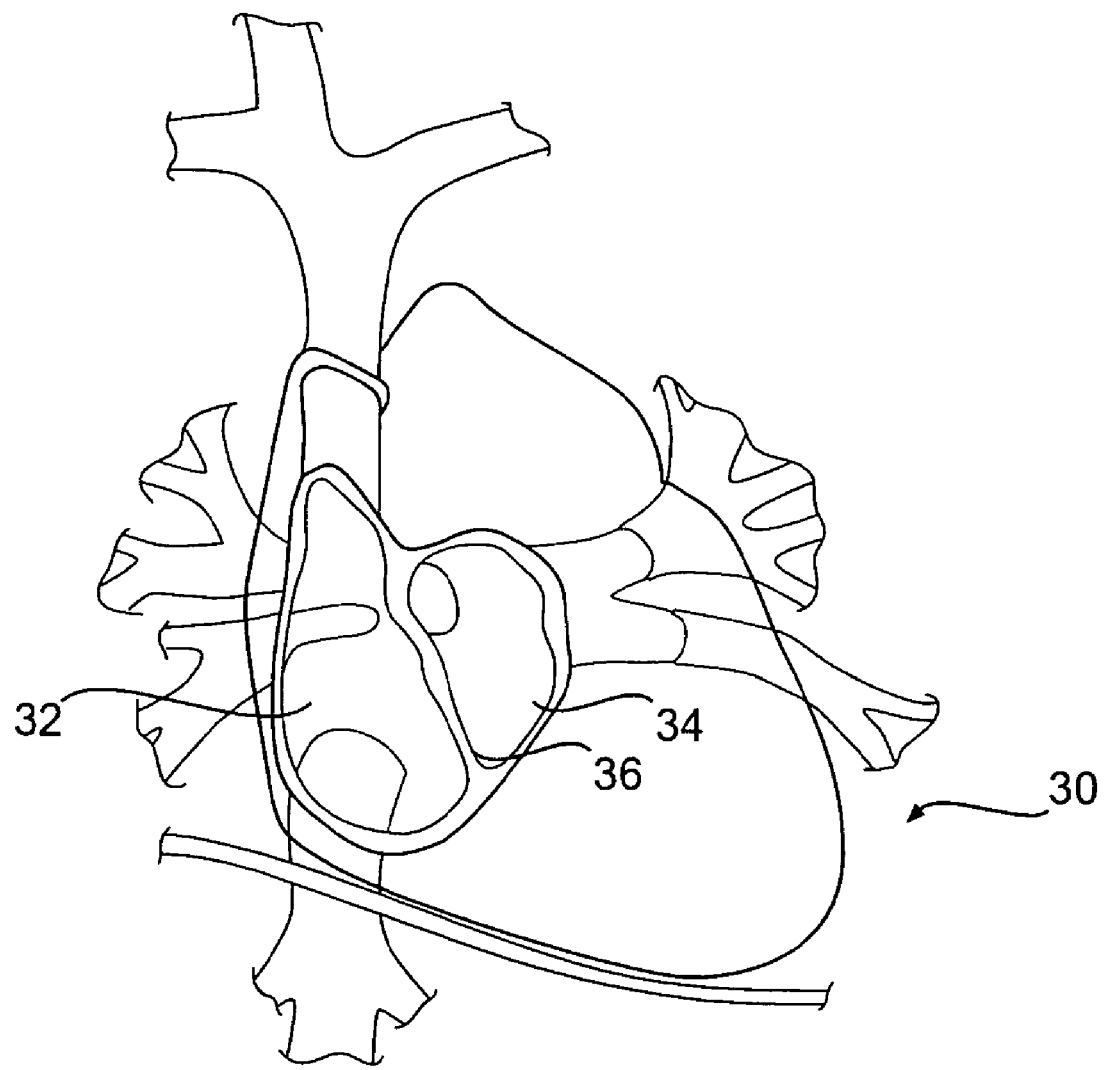
FIG. 3 illustrates a cross-sectional view of the heart area of a patient where the implanted device of the invention may be employed, including the left and right atrium and the crossing of veins at the posterior septum.

FIG. 3 illustrates a cross-sectional view of the heart area of a patient where the implanted device may be employed, including the left and right atrium and the crossing of veins at the posterior septum. The heart 30 has a right atrium 32 and a left atrium 34, which are divided by the septum 36. As described in more detail herein, it may be advantageous to locate and/or anchor the implantable sensor chip 20 at the septum 36 separating the right atrium 32 and the left atrium 34, such that a portion of the sensor 20 extends into the chamber to be sensed, e.g., the left atrium 34. The implantable device may work as a short-term implant as well as a long-term implant. Furthermore, an embodiment of the invention may be implanted at the "Waterston's groove" near the access of the pulmonary vein or any other locations of the heart or in larger vessels near the heart chosen by the doctor. The implantable sensor chip 20 also may be designed to facilitate ready removal of the device if medically necessary.

Figure 4:
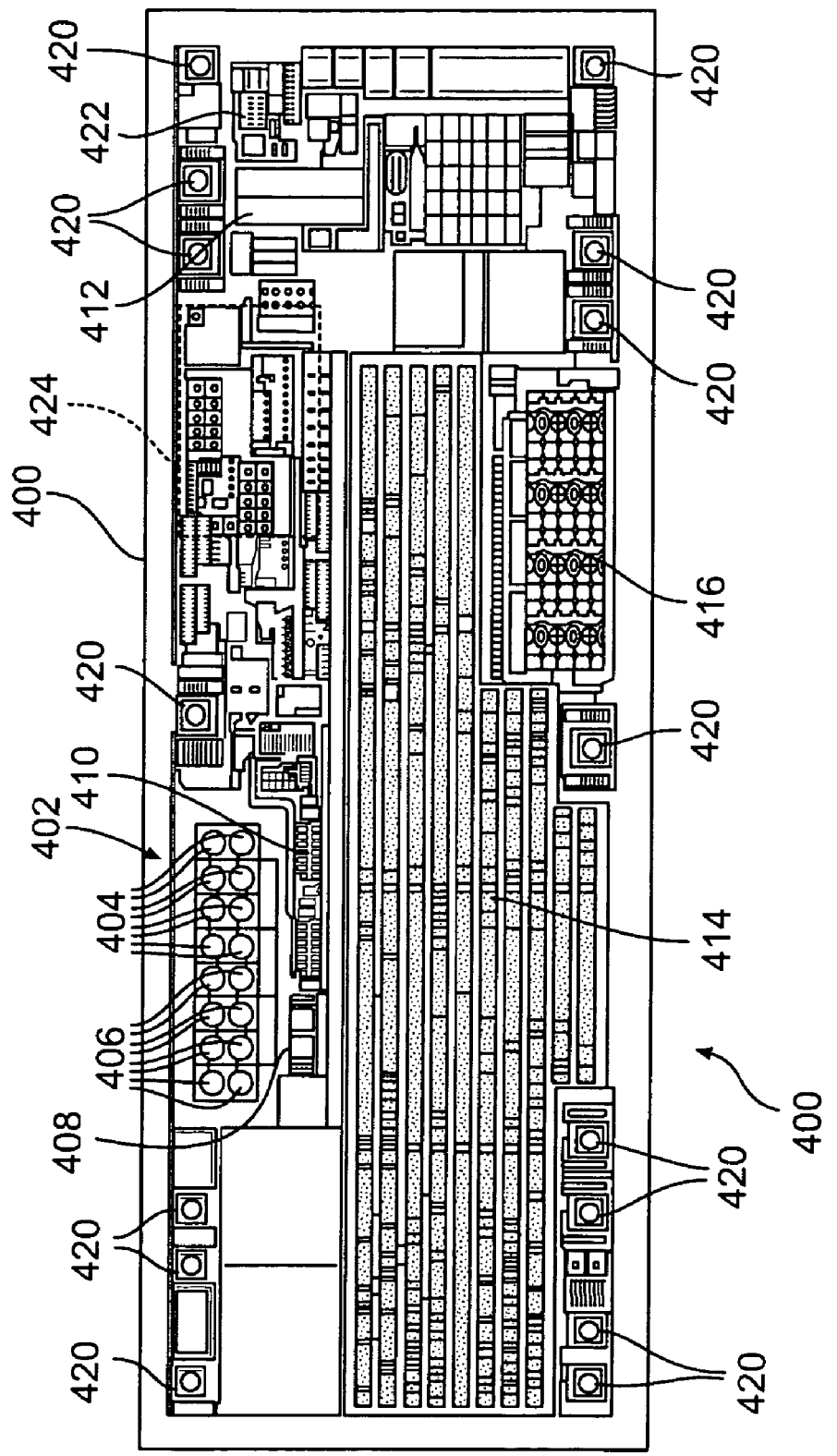
FIG. 4 illustrates a greatly enlarged, plan view of a substantially rigid ASIC constructed according to principles of the invention for sensing intra-cardiac pressure and temperature including active and passive, capacitive membrane sensing elements and on-chip electronics for digital signal processing and telemetrical power supply.

FIG. 4 illustrates a substantially rigid sensor ASIC constructed according to principles of the invention for sensing intra-cardiac pressure and temperature in any of the embodiments of the invention. The ASIC 400 contains pressure sensing elements 402, such as eight passive sensors 404 and eight active sensors 406, temperature sensor 408, an analog-to-digital (A/D) converter 410, data transmission circuitry 412, power conditioning circuitry including components such as smoothing and resonance capacitors (not shown), a digital state control 414 including a code redundancy check for secure data transmission and memory 416, such as Electrically Erasable Read-Only Memory (EEPROM) cells, for unit identification, which are components known in the cart. An example of the suitable ASIC structure is described in U.S. Pat. Nos. 5,321,989 and 5,431,057, the contents of which are expressly incorporated by reference in their entirety.

According to the principles of the invention, the ASIC 400 should be an extremely small and lightweight chip to avoid placing undue stress on the heart and/or producing turbulent flow in the heart chamber(s). For example, an ASIC particularly adapted for use in the embodiments described herein as being implanted during open catheter procedure should weigh less than fractions of a gram, have a surface area of less than or equal to about 10 mm$^2$ per side, and a thickness of about ¼ mm to about 1 mm. In one advantageous embodiment, the ASIC may be about 2 mm wide by 5 mm to 8 mm long by about 250 to 800 microns thick. According to an embodiment of the invention, it may be advantageous to have the ASIC 400 be no more than about 2 mm wide to facilitate delivery of a sensor system including the ASIC 400 via a catheter. Moreover, it may be desirable to break the chip into two or more parts, as described subsequently. Other dimensions may also be used depending upon the particular application or location in the cardiovasculature where the sensing will occur and depending upon the delivery method. In general, the dimensions of the ASIC 400 may range from about 1.5 mm to about 8 mm long, about 0.6 mm to about 2.5 mm wide, and about 0.2 mm to about 1.3 mm high. Other dimensions, such as an ASIC that is substantially square, may also be used.

In the embodiment of the invention shown in FIG. 4, the ASIC 400 includes sixteen capacitive pressure sensors cells 402, eight of which are active pressure sensors 406 and provide pressure data, and eight of which are passive pressure sensors 404 and act as an internal reference. The pressure sensor cells 402 may include minute, flexible membranes that are housed within the substantially rigid ASIC structure as shown schematically in FIG. 5. Specifically, the active pressure sensors 406 have flexible membranes 424 and passive pressure sensors 404 have flexible membranes 426. The membranes 424 of the active pressure sensors 406 are distortable based on the level of cardiac blood pressure. The distortion may be mainly in a direction generally perpendicular to the planar top surface of the ASIC 400. The distortion may be determined based on capacitive measurements or by use of distension measuring tapes. By way of one specific exemplary embodiment, the sixteen capacitive pressure sensing elements 402 of the ASIC 400 may each be about 96 microns in diameter.

As the pressure changes in the heart, the capacitance measured in the pressure sensors 402 changes. The pressure sensors 402 generate signals based on the change in capacitance, and thus indicative of the pressure in the heart. As will be described below, the signals preferably are processed by components located in or on the ASIC 400 and transmitted to an external reader.

Figure 5:
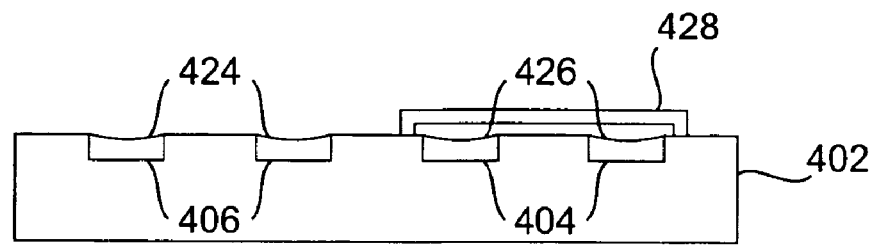
FIG. 5 is an enlarged, cross-sectional view of the ASIC of the invention showing some of the active pressure sensors and passive pressure sensors.

Thus, the blood pressure measuring process may be a capacitive pressure measurement process via measuring membranes 424, 426 that are integrated into the ASIC 400, such as the planar top surface of the chip as shown in FIG. 5. The ASIC 400 may have a substantially inflexible, substrate made of silicon that cannot be folded or rolled up. The thin, but mechanically inflexible substrate creates a mechanically stable device providing a substantially rigid structure to house the measuring membranes 424, 426 as shown in FIG. 5. Changes in the geometry of the ASIC 400, such as twisting due to blood turbulences, may be avoided due to this substantially rigid, chip-based configuration, even when the ASIC 400 is exposed to turbulent, blood flow. Thus, the implanted ASIC 400 provides a durable device capable of withstanding the internal environment of the heart and other locations in the cardiovasculature without producing dangerous stresses within the heart.

Numerous small membranes 424, 426 having relatively small dimensions (e.g., a diameter of less than 0.2 mm) may be used as capacitive pressure sensors. Such small dimensions may result in membranes 424 that are less vulnerable to mechanical forces, such as the force of blood flow within the heart, and therefore more reliable.

The ASIC 400 contains mechanical and electrical elements that are subject to wear and need drift compensation to obtain measurements of suitable quality and reliability for their intended cardiovascular uses. Drift in a sensor may occur as time passes and physical properties of the structure change. Over time and usage, changes in electronics in a chip may effect the measurements. Further, when a pressure sensor uses a membrane, the membrane may sag in the middle as it ages. The capacitance at the pressure sensor membrane varies based on the change in position of the pressure sensor membrane. These changes, unrelated to the change in blood pressure, may alter the true value of the measurements being sensed. Drift compensation is particularly important in an intra-cardiac long-term pressure sensor.

The drift compensation scheme employed in ASIC 400 should reduce or eliminate the effects of the change in the physical properties of the ASIC 400. According to the principles of the invention, the drift of the pressure values obtained from the sensor chip 400 may be minimized to a value of about 5.0 mm Hg/year to about 2.5 mm Hg/year or even smaller than 1 mm Hg/year.

In accordance with drift compensation principles of the invention, a plurality of active sensors 406 and a plurality of passive sensors 404 are provided, such as eight of each. According to an embodiment of the invention, the structure of the active sensors 406 and the structure of the passive sensors 404 are identical. However, as illustrated in FIG. 5, the membranes 424 of the active sensors 406 are open to the sensing environment (e.g., a heart chamber) for sensing pressure, while the membranes 426 of the passive sensors 404 are isolated from the environment, e.g., by placing a glass layer 428 or other suitable material over the surface of the membrane 426 so that pressure in heart will not affect the passive sensors 404. Both the active sensors 406 and passive sensors 404 are affected substantially the same by age, usage and sagging and any other effects of the environment. Using the passive sensors 404, the ASIC 400 may determine how much of the change in position of the pressure sensor membrane 426 is effected by the age and sagging. The change in capacitance based on the change in position of the passive pressure sensor membrane 426 is determined. This amount is then used to offset the change in capacitance measured in the active pressure sensor membrane 424. This system allows the change in capacitance due the pressure within the heart to be more accurately determined. Compensating for drift may allow a doctor or patient to better determine short term (e.g., days, weeks) trends in pressure within the patient, such as the heart.

Figure 6:
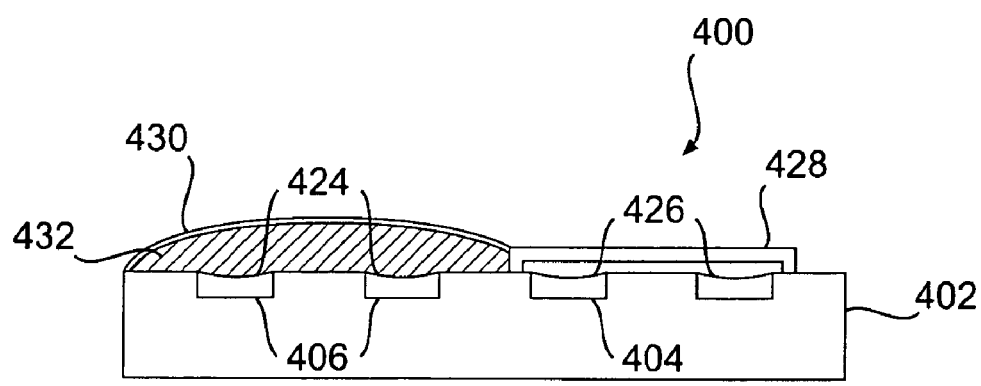
FIG. 6 is an enlarged, cross-sectional view of the ASIC of the invention showing a pressure transmitting gel or fluid between a sheathing and the active pressure sensors.

The implantable sensor chip, which may include the ASIC 400, a connector and an antenna, may be completely encapsulated within a seamless biocompatible sheathing (not shown in FIGS. 5-6). The material areas around the measuring membranes 424 maintain their flexibility after encapsulation to allow transmission of the pressure to the measuring membranes 424. The biocompatible sheathing will be described in greater detail below.

FIG. 6 is a cross-sectional view of the ASIC 402 of the invention with a gel or fluid between a sheathing and the active pressure sensors 406. As described above, a glass substrate 428 or other suitable material isolates the passive pressure sensors 404. A liquid or gelatinous pressure transmitting medium 432 is used between sheathing 430 and the active pressure sensors 406. As will be described below, this liquid or gelatinous medium 432 may improve the measurement or reception of blood pressure values within the chamber to be sensed, e.g., within the left atrium. Even though fibrous tissue or plaque may grow in the area of the implant over time (e.g., months or years after the implantation), encapsulating the pressure sensors within a separate gel-filled membrane may allow reliable measurement values to still be obtained.

For example, endothelialization may result in endothelia being deposited on the surface of the sensor chip. If endothelia and/or plaque are deposited on the surface of one of the active pressure sensors, or on the biocompatible sheathing at the surface of one of the active pressure sensors, pressure measurement readings may be adversely affected. One way to reduce such an effect is to coat the sheathing and/or sensors with a drug, e.g., heparin, to reduce or eliminate endothelia. However, such treatments may not always be effective.

Thus, as illustrated in FIG. 6, the surface of the active pressure sensors 406 are coated with a gel or fluid 432 and encapsulated in the membrane 430. In this manner, endothelia growth or plaque on the membrane 430 directly over the surface of one of the active pressure sensors 406 will have a reduced or negligible effect on the pressure sensor measurement, as the pressure is transmitted via the endothelia growth and the membrane 430 through the gel/fluid 432 to the active pressure sensors 406. Further, plaque growth and/or endothelialization on the entire surface would still allow pressure sensing measurements to be obtained, as the pressure exerted on the endothelia is transmitted via the gel/fluid 432 to the active pressure sensors 406. In particular, the gel/fluid filled membrane 430 may function to integrate the change in pressure over a larger area than the individual active pressure sensors 406 themselves. This minimizes the effects of endothelialization and/or plaque adherence to the sheathing 430. Although sheathing 430 is shown as only covering the gel/fluid 432, it is understood that the sheathing 430 or other sheathings could cover part or all of sensor chip 400, as described below.

The ASIC 400 may also determine the waveform of a heart beat. The waveform of a heart beat may be measured by taking a large number of measurements, e.g., 50 to 100 per second of pressure at a position in the cardiovascular system, such as in the heart. A graph of the pressure values as a function of time is plotted. Using mathematical algorithms known in the art, the waveform of the heart may be calculated based on the graph.

As described above, the ASIC 400 includes an A/D converter 410. As is known in the art, the pressure sensors 402 provide analog signals indicative of the pressure in the heart. The A/D converter 410 converts the signals from the pressure sensors 402 to digital signals.

Thus, the transmission and digitizing of measurement values into appropriate signals in the invention is preferably carried out within or very closely adjacent to the heart chamber or chambers to be sensed, such as the left and/or right atrium and/or the left or right ventricle, and most preferably are processed inside the ASIC 400. Using a fully digital system may result in greater accuracy of the readout. In an analog system, where the amplitude of the signal is proportional to the pressure reading provided by the sensors, the value of pressure recorded by an external reader depends upon the distance between body and reader. As a result, either the distance from the body to reader must be very tightly controlled, or the accuracy of the system will suffer. According to the invention, the distance from body to reader has little or no effect on the pressure value measurement received due to the use of a digital signal and to processing the signals at or very near the sensor. This may make the system more robust and accurate than analog systems, and may further reduce negative effects on the accuracy of measurement due to a change in the distance between the internal coil and the external coil, such as due to movement of the handheld reader. This feature may be especially important for daily use by older patients or those with impaired muscular/motor coordination In addition, the fully digitized data can be handled for more easily by data transmission systems, making the external readers compatible with computer, Internet and telemedicine interfaces. For example, highly accurate pressure sensors and a 9-bit analog-to-digital converter may impart high resolution to the sensing systems, where an accuracy of about +/−2 mm Hg or less may be achieved.

Further, digitization at the ASIC 400, as opposed to analog signal transmission via an antenna before digitization, may avoid interference issues from other, unrelated RF sources. In prior devices, analog signals are sent from the sensor to the antenna structure via a wire. By processing and converting the analog signals to digital signals prior to transmission over the wire to the antenna, the system may avoid analog interference that may be induced in the wire by external RF signals and noise, such as radio broadcasts, electronics, and the like.

The ASIC 400 measures pressure at the pressure sensing elements 402 and transfers the absolute pressure signals to an external reader. A pressure value is calculated from the difference of absolute pressure value, measured with the ASIC 400, and the atmospheric pressure surrounding the patient as is well-known in the art. This atmospheric pressure may be measured within the external reader, which is normally in the surrounding environment of the patient.

The operation of the ASIC 400 is based on the interaction between a connected antenna and an external reader according to well-known principles of transponder technology. Therefore, no internal power source is required. The ASIC 400 and the external reader may be tuned so that continuous measurements, e.g. up to 120 single measurements per second, may be processed and transmitted. As described above in FIG. 1, the total system may be programmed so that measurements are taken and stored in given intervals or at defined time periods. Retrieval, monitoring, and recording of data may be possible at any time.

According to an embodiment of the invention, the ASIC 400 consists of a single integrated chip; however, a dual chip may also be used as described above. All relevant functions and components for the measuring process, digitizing, identification number transmission, power supply, and telemetric data transmission are integrated into the single integrated chip. As described above, the ASIC 400 may contain a specific identification number, as well as a chip specific calibration file and further circuit and storage components. Alternatively, the circuit components may also be placed on two or more chips, e.g. if sensing in separate locations is desired. For example, a first chip may have the active and passive pressure sensing membranes and the analog to digital conversion circuitry, and a second chip may have the other circuitry.

The ASIC 400 may be formed from a single complementary metal oxide semiconductor ("CMOS") chip to produce a smaller implantable device then with other methods, and help minimize power use and maximize measurement accuracy reliability. Since the consumption of power produces heat, minimization of power may be desirable in implantation applications. In a one-chip solution, the ASIC 400 may be highly resistant to mechanical or electrical interference from the outside, as there is no interaction between multiple chips.

The power consumption of the chip may be low, so that if an increase of temperature occurs in the course of inductive/transponder related power insertion, difficulty in measuring or data transmission may be reduced or avoided. The optimized circuit design may result in a very low power consumption, such as only about 210 microwatts at about 3 volts DC. The sampling rate may be about 20 to about 120 Hz. The high integration factor of the logic circuit combined with the high speed of data transmission may allow the use of a very secure data transmission protocol, thereby addressing concerns of the regulatory authorities.

An integrated temperature sensor 408 may be provided in the ASIC 400 to allow for temperature sensing as shown in FIG. 4. The temperature sensor 408 may use the circuit in the ASIC 400 and base the temperature measurement on current characteristics within the circuit, thereby determining the temperature in the heart based on the temperature based current characteristics within the ASIC 400. Each ASIC 400 may be individually calibrated to determine its current characteristics (magnitude, frequency, etc.) at a given temperature (e.g., body temperature). As the temperature changes, the current characteristics within the ASIC 400 change. Using the information on the current characteristics and the specific calibration determination for the ASIC 400, the temperature at a particular time can be determined based on current characteristics at that time. The raw pressure data must be corrected for temperature and other external and/or internal influences, and calibration information, such as a calibration curve of the embedded chip, may be established for each ASIC 400 or system that implements an ASIC 400. Each ASIC may have a unique identification number to facilitate calibration and use of data as discussed below.

The ASIC 400 includes a data memory 416, such as the EEPROM cells, in which the unique identification number may be stored. This identification number is transmitted telemetrically together with the measurement values. The identification number may be used to determine the appropriate calibration information for an ASIC 400. Also, a single external reader may then be used to interrogate multiple implanted ASICs, as described below.

The unique identification number may be transmitted along with the sensor data to the external reader to allow the external reader to use the correct calibration information to calculate pressure and/or temperature. An external reader (as described in greater detail below), may have a memory to store calibration information for a number of ASICs 400 or systems that implement ASICs 400. The appropriate calibration information is associated the appropriate ASIC 400 or system via the identification number. With the identification number, or other identification indicia, the external reader accesses the calibration information associated with the particular ASIC 400 or system that includes the particular ASIC 400. The data received by the external reader is processed using the appropriate calibration information to achieve more accurate results.

Each ASIC 400 and/or system also may be zeroed prior to implantation. When inside the patient, the system compares the measured pressure to the pressure in a vacuum. Outside the patient, the external reader compares the ambient pressure to the pressure in a vacuum. Pressure inside the heart, as defined by the doctor, is calculated by comparing the difference between the pressure measured inside the heart and the pressure measured outside the patient. Zeroing the ASIC 400 or the system may involve using the ASIC 400 system to measure the pressure outside the patient and comparing this measurement to the pressure obtained by another external device. The difference between these two readings may be stored with the calibration information associated with the ASIC 400 or system and used to adjust future pressure measurements by the ASIC 400 or system once it has been implanted to account for the difference.

Using one or more intracorporal and/or extracorporal transponder coils, an external reader may be used for the power supply of the ASIC. This unit also may be used for telemetric data acquisition. The range for telemetric power supply and data transmission may be from about 3 cm to about 35 cm or other ranges as can be readily determined by a skilled artisan. This range also may depend on the distance between the external reader and the implanted antenna and the size of the antennas Measurement data are processed and preferably are digitized on the ASIC 400 for transmission from the sensor chip to the interior transponder coil. The transmission of the measurement data from the ASIC 400 to the interior transponder coil may be realized via one or more electric conductors, preferably designed as flexible thin wires, embedded in silicone on other nonconducting material. Measurement data are transmitted telemetrically from the interior transponder coil to the external reader. The external reader capacities may be designed for an exterior supply of all power resources which are required for the continuous operation of ASIC 400, including measurements and data transmission.

The ASIC 400 also includes a bi-directional power circuitry 424 for working with the reader to evaluate the strength of the signals sent between the reader and the ASIC 400. The components in the bi-directional power circuitry 424 interact with a reader to ensure that appropriate signal strength and data transmission is achieved. The interaction between the bi-directional power evaluation module 424 and the reader is described in greater detail below with respect to FIG. 35.

Although the ASIC 400 of FIG. 4 has been described in a one chip solution, it is understood that multiple chips may be used to implement the functionality of the invention. By way of example, a first ASIC may include the pressure sensing membranes and digitization circuitry, while the telemetric and transmission circuitry may be located on a second ASIC. Moreover, the multiple chips may be located in different portions of the heart to provide information about the absolute pressure at different locations within the heart, as well the differential pressure between different locations. By way of example, the first ASIC may be located in the left atrium and the second ASIC may be located in the right atrium. Such a chip configuration may be similar to that found in FIG. 34. Other configurations may also be used.

FIGS. 7 and 8 schematically illustrate an embodiment of an implantable sensor chip 700 of the invention including a substantially rigid sensor chip connected at two ends to a substantially rigid substrate 708 having a cut out. A sensor chip 702, such as ASIC 400, includes pressure sensing membranes 704 and four spaced chip bond pads 706. A substantially rigid substrate 708 having an aperture 710 and bond tracks 712 connected to bond pads 706 are also provided. The substrate 708 is configured in a spaced apart relationship to the sensor chip 702. More particularly, the aperture 710 of the substrate 708 is located substantially opposite of the capacitive pressure membranes 704 of the sensor chip 702 so pressure from the blood surrounding the device may be transmitted readily to the pressure membranes 704. A pressure transferring material (not shown) may be located at the aperture 710 to ensure that pressure from the blood is transferred to the pressure membranes 704.

The sensor chip 702 and the substrate 708 may be configured in a fixed relationship, so that the distance, or offset, between the sensor chip 702 and the substrate 708 does not change. The chip bond pads 706 may be connected to the substrate bond pads 712 to fix the distance between the sensor chip 702 and the substrate 708. As shown in the embodiment of FIGS. 7 and 8, the sensor chip 702 and the substrate 708 both have four bond pads. However, it is understood that other amounts of bond pads may also be used.

At least one of the substrate bond pads 712 may be elongated in the form of a track to facilitate connection to an electrical wire 714 that connects to an antenna (not shown). Electrical wire 714 is connected to the substrate bond pad 712 by any conventional method, such as by using heat and pressure. Connecting the electrical wire 714 to a substrate bond pad 712, as opposed to being directly connected to chip 702, may reduce or eliminate damage to or malfunction by the sensor chip due to the connection process. The electrical wire 714 is electrically connected to the sensor chip 702 via the electrical connection between the substrate bond pad 712 and the chip bond pad 706.

Figure 9:
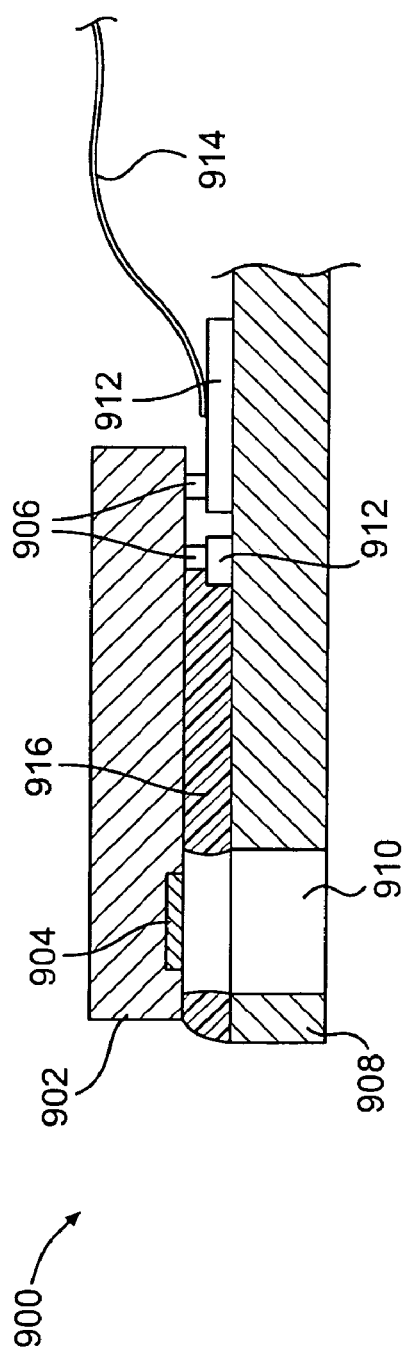
FIGS. 9 and 10 schematically illustrate a cross-sectional and top plan view, respectively, of another embodiment of an implantable sensor chip of the invention including a substantially rigid ASIC connected at one end to a substrate having a cut out.
Figure 10:
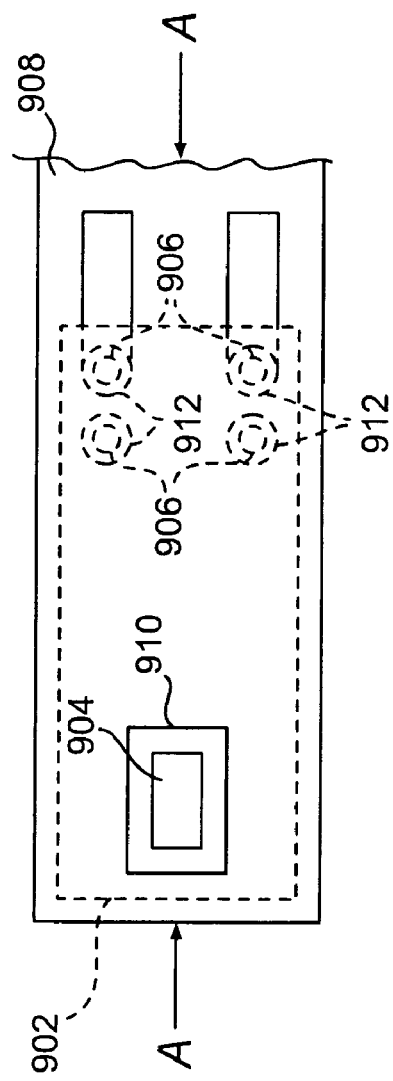

FIGS. 9 and 10 schematically illustrate another embodiment of an implantable sensor chip including a substantially rigid sensor chip connected at one end to a substantially rigid substrate having a cut out. The device 900 of FIGS. 9 and 10 has similar components and operation to the device 700 illustrated in FIGS. 7 and 8. However, device 900 has chip bond pads 906 located in generally close proximity to each other at one end of the sensor chip 902. In addition, the substrate bond pads 912 are generally located in close proximity to each other on the substrate 908. When the chip bond pads 906 and the substrate bond pads 912 are connected, the sensor chip 902 and the substrate 908 are fixed at one end, with the other free end being supported in a cantilevered manner. This arrangement of chip bond pads 906 and substrate bond pads 912 may reduce stress on the sensor chip 902, as changes in the size of the substantially rigid substrate 908, such as due to thermal expansion, may have less of an effect on the sensor chip 902 due to the location of the chip bond pads 906 on the sensor chip 902.

The device 900 may further include a flexible filler material 916 located between the sensor chip 902 and the substrate 908. As shown, the filler 916 may be located throughout the area between the sensor chip 902 and the substrate 908 except at the aperture 910 that is opposite the capacitive pressure membranes 904. Filler 916 may be any flexible material that can provide support to reduce or eliminate movement in the offset direction between the sensor chip 902 and the substrate 908. The filler 916 may be the same material used to surround the implanted device 900, such as a biocompatible material like silicone or other similar material.

Figure 11:
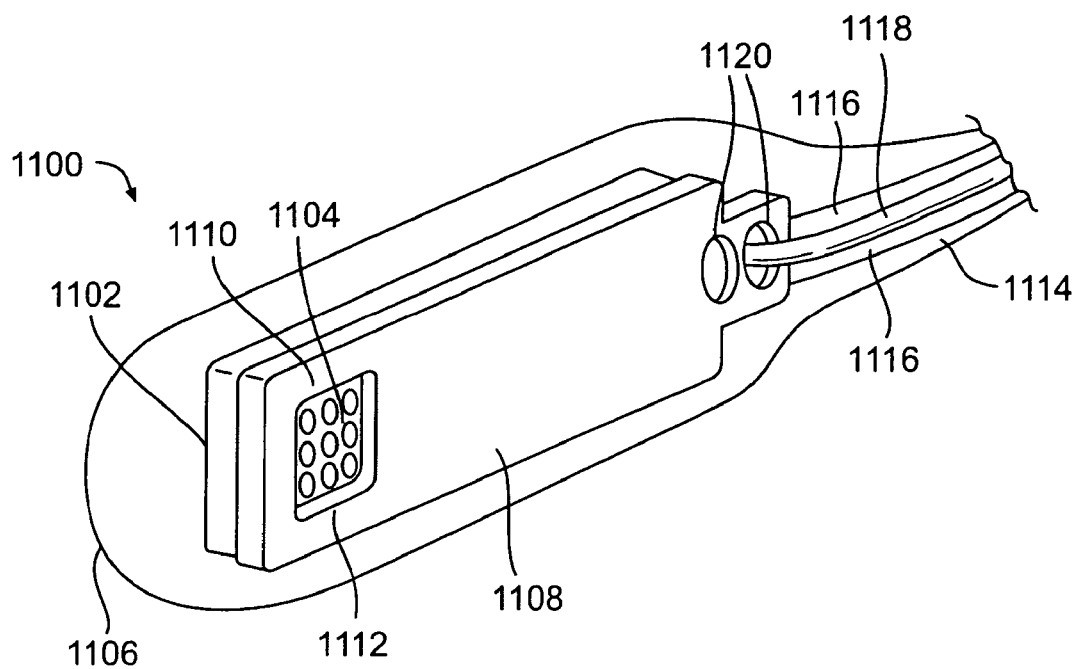
FIG. 11 is a perspective illustration of the implantable device of FIGS. 7 and 8 or 9 and 10, showing an electrical wire and filament core connection between the ASIC and the antenna.

FIG. 11 is a perspective illustration of an implantable sensor chip such as the FIGS. 7 and 8 or FIGS. 9 and 10 embodiments showing the electrical wire and core filament connection to the ASIC and antenna. The device 1100 includes a substantially rigid sensor chip 1102 having pressure membranes 1104, and a substantially rigid substrate 1108 with an aperture 1110 exposing the pressure membranes 1104. A pressure transmitting material 1112, such as a liquid or gelatinous material, is located within the aperture 1110 to transmit pressure from the blood to the pressure membranes 1104. The entire device 1100 is enclosed by a biocompatible sheathing 1106, such as silicone. In addition, the sheathing 1106 can also be used as the pressure transmitting material 1112 within the aperture 1110.

Substrate 1108 may further include connector holes 1120 for facilitating attachment of an antenna connector 1114 to the substrate 1108 and the sensor chip 1102. The connector 1114 includes electrical wires 1116 and a filament core 1118, such as nylon. Electrical wires 1116, which may be formed of gold cable, or other appropriate material, provide an electrical connection between the sensor chip 1102 and an antenna (not shown). Electrical power from the antenna may be conducted via the electrical wires 1116 to the sensor chip 1102 for powering the sensor chip 1102 to obtain measurements. Signals, such as pressure measurements and identification indicia, may be transmitted over the electrical wires 1116 from the sensor chip 1102 to the antenna for transmission to a reader. The filament core 1118 provides strength to the connector 1114 to reduce or eliminate strain on the connection between the substrate bond pad (not shown) and the electrical wires 1116. By way of example, this type of strain relief may be implemented in a connection between two implanted chips or between the chip and the coil. The filament core may be made of nylon or other similar, synthetic flexible material that does not conduct electricity and has a low coefficient of thermal expansion. This connection will now be described in greater detail below with reference to the examples of FIGS. 12-14.

Figure 12:
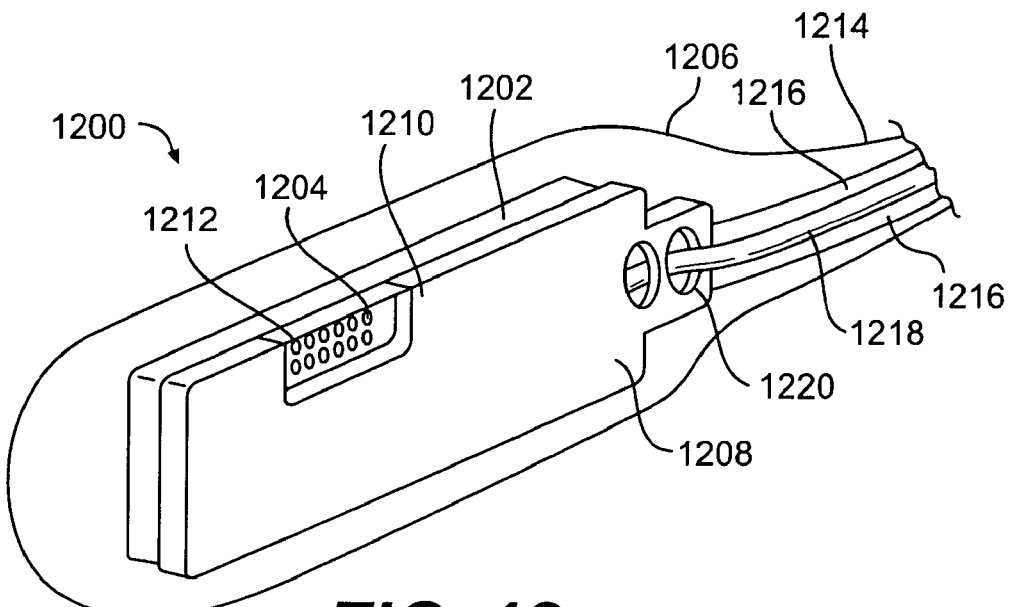
FIG. 12 illustrates a perspective view of the implantable sensor chip of the invention with a cut out located at an edge of the substrate.
Figure 13:
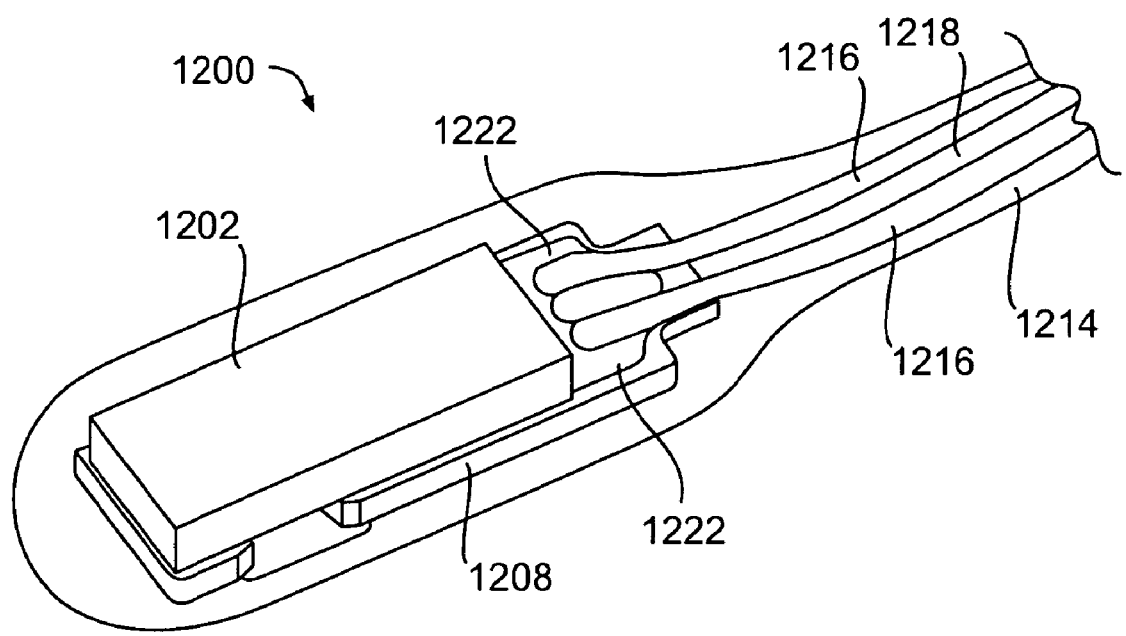
FIG. 13 is a perspective view showing the electrical wire and filament core connection of the FIG. 12 embodiment.

FIGS. 12 and 13 illustrate an implantable sensor chip 1200 with a cut out located at an edge of the substantially rigid substrate, including a cable and core filament connection. The implantable device 1200 includes a substantially rigid sensor chip 1202 having pressure membranes 1204. In this embodiment, the capacitive pressure membranes 1204 are located near the edge of one side of the sensor chip 1202. The device 1200 further includes a substantially rigid substrate 1208 having connector holes 1220 and a cut out 1210 opposite of the pressure membranes 1204. A pressure transmitting material 1212 is located within the cut out 1210 to transmit pressure from the blood to the pressure membranes 1204. The device 1200 is surrounded by a biocompatible sheathing 1206, such as silicone. According to a preferred embodiment of the invention, the pressure transmitting material 1212 may be the same as the sheathing material 1206.

The device 1200 further includes a connector 1214 which includes electrical wires 1216 and a filament core 1218. The electrical wires 1216, which may be formed of gold, or any other suitable similar material, connect to substrate bond pads 1222, and the substrate bond pads 1222 are connected to chip bond pads 1224. This results in an electrical connection between the electrical wires 1216 and the sensor chip 1202. The filament core 1218 may be attached directly to the substrate 1208, such as by an adhesive. As shown in FIG. 13, the filament core 1218 is threaded through the connector hole 1220 for attachment to the substrate 1208 such that the electrical wires 1216 have extra slack when the filament core 1218 is pulled straight. This configuration may reduce or eliminate the strain on the connection between the electrical wires 1216 and the substrate bond pad 1222 when there is movement of either the connector 1214 or the substrate 1208. Moreover, such methods for providing strain relief may be used in embodiments employing two or more chips such as relief to a wire connecting two chips. Any other method providing for strain relief known in the art of electrical wires 1216 may also be used.

Figure 14:
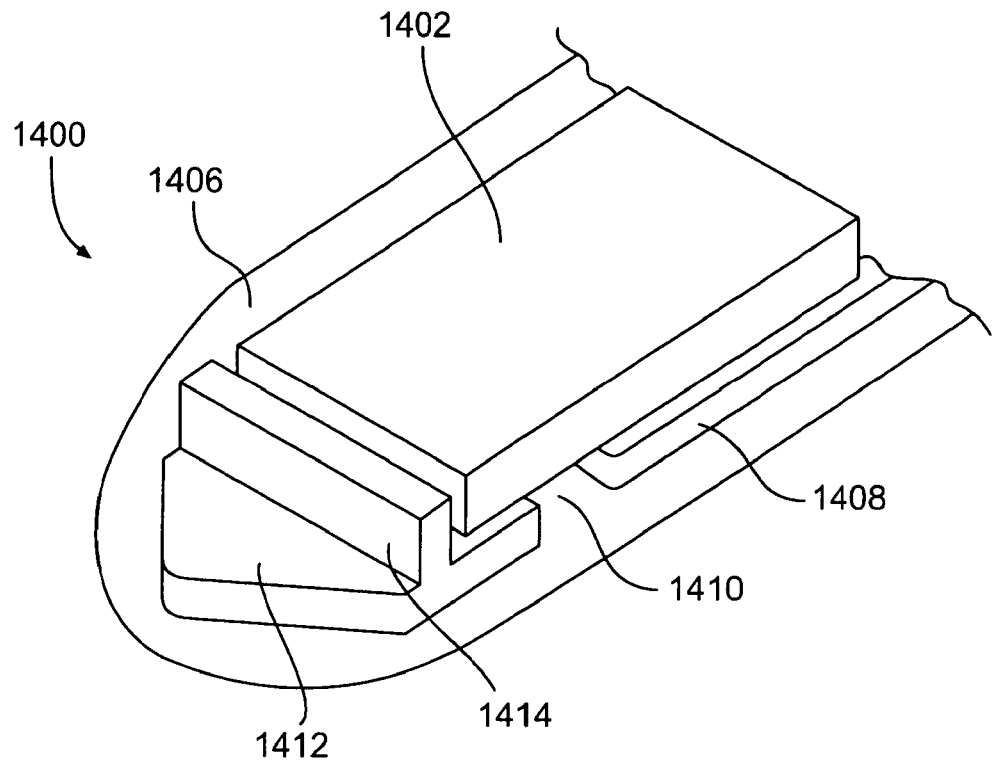
FIGS. 14 and 15 schematically illustrate yet another embodiment of an implantable sensor chip of the invention having a cut out located at an edge of the substantially rigid substrate and a protective barrier wall located at one end.
Figure 15:
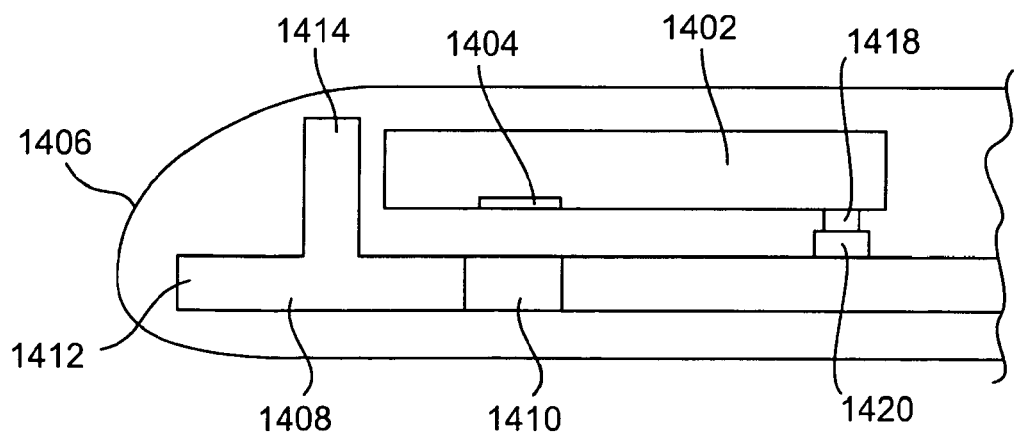

FIGS. 14 and 15 schematically illustrate an implantable sensor chip with a cut out located at an edge of the substrate and a protective barrier wall located at one end of the substrate. The device 1400 has a substantially rigid sensor chip 1402 having capacitive pressure membranes 1404 (shown in FIG. 15). The device 1400 further includes a substantially rigid substrate 1408 having a cut out 1410 located substantially opposite the pressure membranes 1404. A chip bond pad 1418 on the sensor chip 1402 is connected to a substrate bond pad 1420 of the substrate 1408 in a conventional manner. The device 1400 is encapsulated in a biocompatible sheathing 1406.

The substrate 1408 includes a barrier wall 1414 that may be substantially perpendicular to the plane of the substrate 1408. The height of the barrier wall 1414 may be such that the top of the barrier wall 1414 is at or above the top of the sensor chip 1402 when it is attached to the substrate 1408. The barrier wall 1414 may provide additional protection to the chip sensor 1402, such as preventing the sharp ends of the chip 1402 from wearing or puncturing the sheathing 1406. In addition, a front portion 1412 of the substrate 1408 shaped like an arrow is located beyond the barrier wall 1414 and is tapered to reduce or eliminate the effects of blood turbulence on the chip sensor 1402, as well as aid in the implantation of the device 1400 within the heart. The front portion 1412 may be designed in such a manner as to aid specifically in implantation of the device 1400 via a catheter or other minimally-invasive procedure. This may occur when the tapered portion 1412, and thus the device 1400, is inserted into the heart. The edges of the barrier wall may be slightly rounded (not shown in the drawings) to avoid any wearing or puncturing of the sheathing. Although not shown, it is understood that a pressure transmitting material and/or a filler material may be used with the device 1400.

Figure 16:
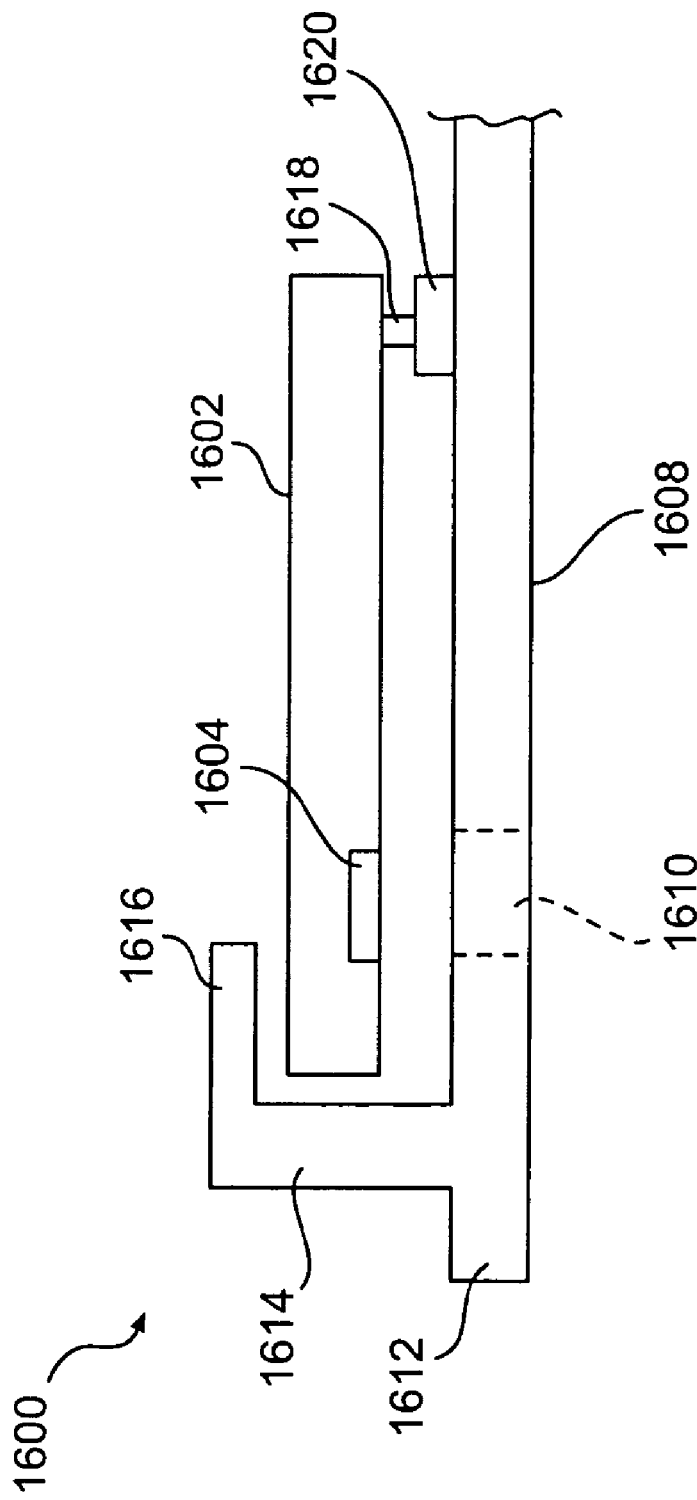
FIG. 16 schematically illustrates a cross section view of a further embodiment of the protective barrier wall of the invention.

FIG. 16 schematically illustrates a cross sectional view of a further embodiment of a barrier wall formed as an end cap at one end of the sensor chip. The device 1600 has a sensor chip 1602 having capacitive pressure membranes 1604. The device 1600 further includes a substrate 1608 having a cut out 1610 located substantially opposite the pressure membranes 1604. A chip bond pad 1618 on the sensor chip 1602 is connected to a substrate bond pad 1620 of the substrate 1608 in a conventional manner. The device 1600 may also be encapsulated in a biocompatible sheathing (not shown in FIG. 16).

The substrate 1608 may include a barrier wall 1614 that is substantially perpendicular to the plane of the substrate 1608, as in the prior embodiment. The height of the barrier wall 1614 may be such that the top of the barrier wall 1614 is at or above the top of the sensor chip 1602 when it is attached to the substrate 1608. In addition, the barrier wall includes a top cover 1616 extending inwardly from the top of the barrier wall 1614 substantially parallel to the substrate 1608 over the sensor chip 1602 to provide protection to the top of the sensor chip 1602. Although shown in FIG. 16 as extending over only a small area of the sensor chip 1602, it is understood that the barrier top cover 1616 could extend further, including along the entire length of the sensor chip or beyond. The barrier wall 1614 and the barrier top cover 1616 may provide additional protection to the chip sensor 1602 and the sheathing as discussed above. More specifically, the barrier top cover 1616 may inhibit damage to the sheathing 1606 that could occur by rubbing of sharp edges of the chip sensor 1602 against the sheathing material 1606. In addition, a front portion 1612 of the substrate 1608 is located beyond the barrier wall 1614 and may be tapered to reduce turbulence, as well as aid in the implantation of the device 1600 within the heart, also as discussed above.

Figure 17:
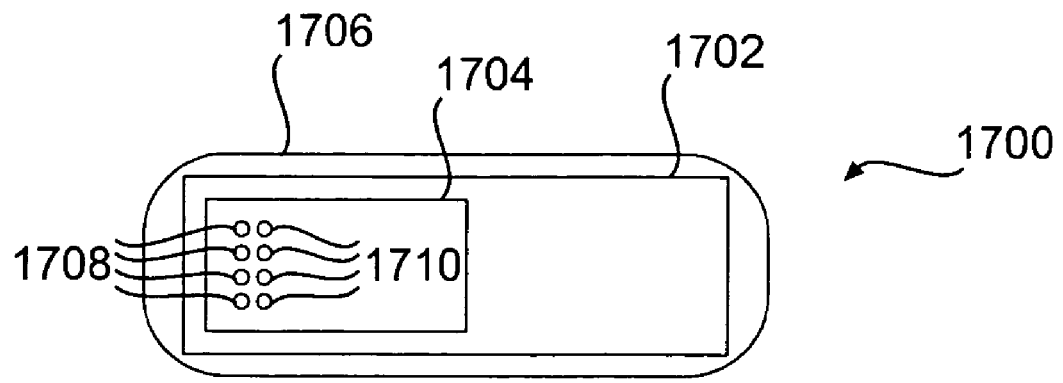
FIG. 17 schematically illustrates a sensor chip of the invention encased in a biocompatible sheathing.

FIG. 17 schematically illustrates a sensor chip of the invention encased in a biocompatible sheathing. A sensor chip 1700 includes an ASIC 1704 positioned on a substantially rigid substrate 1702 and encapsulated in a biocompatible sheathing 1706. The sensor system, i.e., the ASIC 1704, substrate 1702, cable (not shown) and antenna (not shown) may be encapsulated in a biocompatible sheathing such as, silicone, polyurethane or other suitable material. The encapsulation of the system preferably is seamless, i.e., has no break or seam. This reduces or eliminates the risk of contamination or damage to the sensor system structure by fluids within the body. By way of example, the thickness of the encapsulation may be in the range of about 0.01 mm to about 0.8 mm. A seamless sheathing may be obtained by seamless molding or by dipping the entire sensor chip 1700 (sensor ASIC, cable and antenna) into the biocompatible material.

Figure 18:
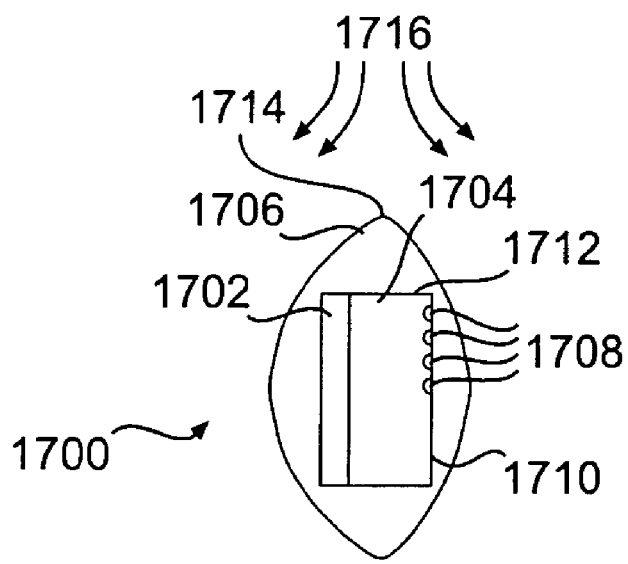
FIG. 18 is a side view of the device illustrated in FIG. 17 illustrating how the shape of the sensor may be configured as a football shape to minimize turbulence and reactionary fluid forces in the heart.

The implanted device may be positioned in heart to minimize turbulence of the blood flow within the heart chamber and reactionary forces. As illustrated in FIG. 18, the sensor chip 1700 may be orientated such that its shortest side, such as side 1712, may be positioned to be in the most upstream position in the blood flow path 1716. This presents the minimum area in the blood flow and reduces and/or minimizes currents and reactionary forces caused by the implanted device 1700. This positioning may be done regardless of location of the pressure sensors 1708 on the chip. As illustrated, the longer sides 1710 of the sensor chip 1700 containing the top surfaces of the capacitive pressure membranes 1708 may be parallel to the blood flow 1716.

As illustrated in FIG. 18, the shape of the sheathing surface 1714 also may be curved or shaped, e.g., similar to the football shape shown in FIG. 18, to further reduce the turbulence caused by blood flow 1716 around the sensor chip. The biocompatible sheathing 1708 may be applied to the implanted device 1700 to form the curved surface 1714. Such curves or other shapes may be designed to minimize hydrodynamic forces.

The encapsulation in a fully biocompatible material, such as silicone may result in very little change in the sensitivity of the pressure sensor. Further, a small offset due to the influence of the encapsulation material may be compensated for during calibration. This may allow, for example, measurements of about +/−2 mm Hg or less.

Figure 19:
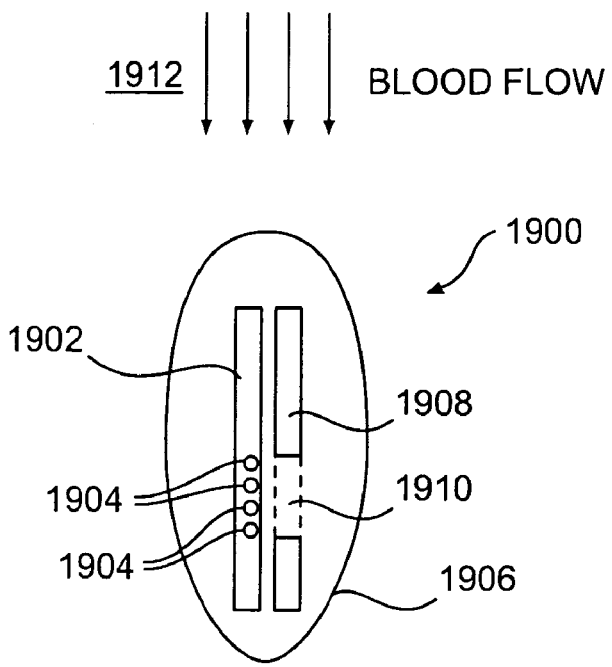
FIG. 19 is a side view of a dual substrate sensor chip of the invention showing how the shape of the sheathing may be configured to minimize turbulence and reactionary fluid forces in the heart.

FIG. 19 is a side view of a dual substrate sensor embodiment of the invention illustrating how the shape of the sheathing may be configured to minimize turbulence and reactionary fluid forces in the heart. The implantable device 1900 includes a substantially rigid ASIC 1902 having capacitive pressure membranes 1904 and a substrate 1908 with an aperture 1910 substantially opposite the pressure membranes 1904. As illustrated, the device 1900 is encapsulated in a sheathing 1906. The sheathing 1906 may be made of a biocompatible material, such as silicone, that is flexible so that the pressure from the blood may be transmitted to the pressure membranes 1904. A pressure transmitting material (not shown) may be placed in the aperture 1910 to aid in transmitting the pressure. The sheathing 1906 may be shaped, such as an oval or football configuration, to reduce or eliminate hydrodynamic forces from the blood flow 1912. Again, the smallest sides of the device are orientated into the upstream portion of 1912 of the blood flow.

Figure 20:
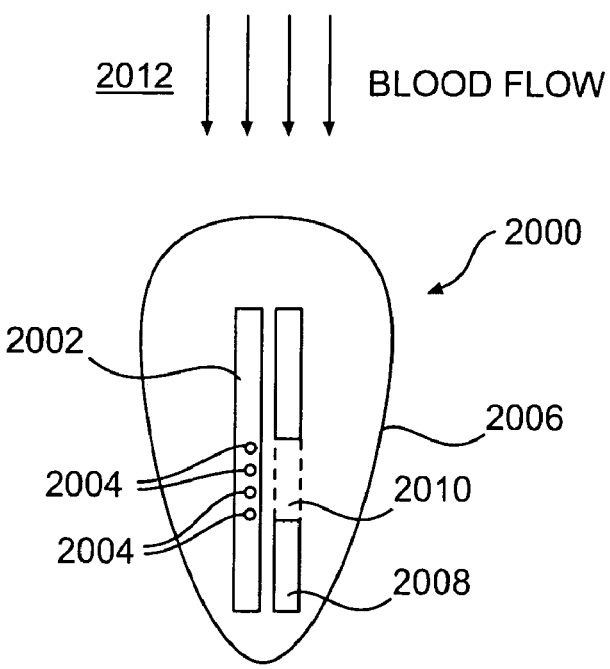
FIG. 20 is a side view of another embodiment of the invention illustrating how the shape of the sheathing may be configured to minimize turbulence and reactionary fluid forces in the heart.

FIG. 20 is a side view of another embodiment of the invention illustrating how the shape of the sheathing may be configured to minimize turbulence and reactionary fluid forces in the heart. The device 2000 has the same components as the FIG. 19 embodiment and is like-numbered. However, in this embodiment, the sheathing 2006 may be shaped, such as in a rounded triangle configuration, to reduce or eliminate hydrodynamic forces from the blood flow 1912.

FIG. 21 illustrates an embodiment of an implantable telemetric measuring device constructed according to principles of the invention, which is particularly adapted for implantation via catheterization in which the sensor chip and the antenna are located on opposite sides of the septum. For purposes of illustration, the implantable device 2100 is implanted into the cardiac septum 36 in a position to sense pressure in the left atrium of the heart, but may be implanted in a position to sense pressure in any heart chamber or other location in the cardiovasculature such as the pulmonary artery or any of the other great vessels. The implantable device 2100 includes a substantially rigid sensor chip 2102, an antenna structure 2106, and a resilient, anchorage structure 2108. The sensor chip 2102 may be an ASIC 2118; similar to any of the ASICs described above, with pressure sensors 2126. The anchorage structure 2108 is used to affix the implantable device 2100 to the heart, such as to the septum 36. The anchorage structure 2108 includes a connection piece 2104, an anchor 2110, and an anchor clip 2112 and a fixing attachment 2130. In the course of the implantation process, the connection piece 2104 is passed through foramen 40 in the cardiac septum 36 and connects the ASIC 2118 and coil 2106 to the heart wall. The connection piece 2104 may be an oblong element made of polyamide plastic. Other materials known in the art may also be used. As shown, the connection between anchor structure 2108 and connection piece 2104 may be done via anchor clip 2112. Other fasteners which provide a mechanical and/or electrical connection between the anchor structure 2108 with anchor 2110 and the connection piece 2104. The connection piece 2104 and sensor chip 2102 may be connected by fixing attachment 2130. The connection piece 2104 may be embedded into a hermetically sealed, biocompatible sheathing, and may fit snugly into the foramen 40 in the cardiac septum 36. While the connection piece shown FIGS. 21 and 22 passes through the ASIC, it is understood that other structure methods for connecting the sensor and antenna to the heart may also be used, including connections that do not pass through the ASIC, such as a flexible wire or the cables between the antenna and the chip.

As shown in the embodiment of FIG. 21, the anchor 2110 and the anchor clip 2112 are connected to one end of the connection piece 2104. The anchor 2110 resiliently engages the antenna structure 2106 and forces the antenna structure 2106 against the septum 36. FIG. 21 illustrates a minimum distance "d" between the anchor structure 2108 and the sensor chip 2102. The minimum distance "d" may correspond to or be slightly less than the thickness of the cardiac septum 36. When an antenna structure 2106 is placed between anchor structure 2108 and sensor chip 2102, the distance "d" may be enlarged based on the width dimensions of the antenna structure 2106.

The antenna structure 2106 may include a coil schematically shown at 2114, an antenna base 2122, and protective sheathing 2124. Coil 2114 provides the antenna for the implantable device 2100, and may be made of a metallic material, such as gold or any other appropriate material. An antenna base 2122 may be provided to support the coil 2114. By way of example, antenna base 2122 may be a plastic material, with the coil 2114 wrapped around the periphery of the antenna base 2122. The sheathing 2124 may be provided around the coil 2114 and the antenna base 2124 to protect the coil 2114 and the antenna base 2124, and may cooperate to help maintain the coil 2114 on the antenna base 2124 by sealing the coil 2114 to the antenna base 2124. The sheathing 2124 may be made of a biocompatible material, such as silicon, and may be designed as an undivided seamless coating, thus encapsulating the connection wire(s) 2132 that connect the antenna structure 2106 to the sensor chip 2102. According to another embodiment of the invention, the sheathing 2124 may also encapsulate the antenna structure 2106, the anchor structure 2108 and the connection piece 2104 between the sensor chip 2102. A suitable coating material, either applied totally or partially to the sheathing, may be used to prevent or reduce endothelialization including the formation of thrombus and/or fibrinogen, such as heparin, or other material known to those skilled in the art.

The coil 2114, which is used in the examples, may be made of one or more electroconductive twisted coils. The coils 2114 may be arranged in one or more layers, and in various shapes. For example, the coils 2114 may be twisted in circular, elliptical or any other geometrical shape. The coils 2114 may be flexible and placed on a foldable or rolled up insulating material, preferably made of synthetic material. The whole coil formation may be designed integrally with the coil base 2122. In addition, thin wires may be used as material for the twisted coils. The coil 2114 may be made of precious metals, such as gold, platinum, iridium, stainless steel, spring steel, or similar material, as is known in the art. The coil 2114 may be made of pure gold, or any other suitable material, to provide both biocompatibility and the necessary degree of electrical conductivity. According to a preferred embodiment of the invention, the coil 2114 and the wire 2132 may be made of the same material, and the wire 2132 may be part of the coil 2114, e.g., the wire 2132 and the coil 2114 are integrally formed. All components of the implantable device 2100, including the coil 2114, the wire 2132, and the anchor structure 1408, may be very small and light weight to avoid strain and irritation of the heart when implanted. Thus, by way of example, the anchor structure 2108 may be made of a light weight plastic, and the coil 2114 and wire 2132 in connector may be made of a relatively thin and lightweight wire material, such as thin gold or other suitable materials.

The number and size of the coils 2114 on the exterior circumference of the antenna structure 2106 are dimensioned in such a way that a telemetric range of at least 45 cm may be achieved. This may be the minimum range for the transmission of measurement data to the extra corporal emitter/receiver unit. By way of example, when the antenna is fixed within or near the heart, the range may be at about 45 cm. However, this required range may change based on various factors, such as the position of the antenna within or near the heart.

As described above, all energy which is required for the acquisition of measurement data may be provided telemetrically by antenna structure 2106. The coil 2114 may be designed as a passive coil. Examples of suitable coils are illustrated in German patents DE 199 45 879 A1 or DE 101 56 469 A1.

The sensor chip 2102 may be implanted so that the pressure sensors 2126 are directed toward the center of the left atrium 34 or other heart chamber or sensing location. As illustrated, after successful implantation of the antenna structure 2106, e.g. using the methods described subsequently, a contact surface 2120 of the sheathing 2124 on the antenna structure 2108 is resiliently pressed against one side of the cardiac septum 36 by the spring-like anchor 2110. This contact may be used to strengthen the fixation of the anchor structure 2108 to the cardiac septum 36. Further, a contact surface 2134 of the sheathing 2124 on the sensor chip 2102 also is resiliently pressed against the opposite side of the cardiac septum 36 by the anchor 2110. Thus, the contact surface 2134 is used as support and fixed to the cardiac septum 36 at the left atrium 34, while contact surface 2120 serves as counter bearing at the right atrium.

As shown in FIGS. 21-22, the sensor chip and the antenna, designed as a passive transponder coil, are arranged separately. In this way, the shape and size of the transponder coil may be independent from the dimensions of the sensor chip. Due to this configuration, the whole implantable device, including the substantially rigid, sensor chip, flexible, transponder coil and electroconductive connection, may be rolled up to a structure with a significantly small diameter. Therefore, the entire telemetric measuring device is suitable for implantation using typical cardiac catheters having narrow lumens, as described subsequently.

FIG. 22 illustrates another embodiment of an implantable telemetric measuring device similar to be FIG. 21 embodiment. FIG. 22 differs from FIG. 21 in that the antenna structure 2106 is placed between the sensor chip 2102 and cardiac septum 36. Therefore, for ease of reference and description, the same reference numerals have been used for the same or similar parts. In FIG. 22, the sensor chip 2102 and antenna structure 2106 are implanted into the left atrium 34, while the anchor structure 2108 is disposed in the right atrium 32.

The anchor structure 2108 and the sensor chip 2102 are connected with a connection piece 2104, which is extends through the foramen 40 in the cardiac septum 36. As in the FIG. 21 embodiment, the mechanical tension that arises from the tension between the sensor chip 2102 and connection piece 2104 produces adhesion used to firmly affix the device to the septum. In FIG. 22, the contact surface 2120 of the sheathing 2124 on the antenna structure 2106 serves as a counter bearing for anchor structure 2108.

FIG. 23 illustrates another embodiment of a pressure sensor that may be used in the devices of FIGS. 21 and 22 according to principles of the invention. FIG. 23 illustrates a second transponder coil 2128 for internal data transmission, which is mechanically and electrically fixed to the sensor chip 2102, such as by metallizations or thin wires. The second transponder coil may obviate the need for connection wire 2132 between coil 2114 and the sensor chip 2102 as shown in FIGS. 21 and 22, because data is transmitted telemetrically from the internal data transponder coil 2128 to the external data transponder coil 2114 and then on to the external reader. Alternatively, the data may be transmitted telemetrically from the internal data transponder coil 2128 to another chip (not shown) and then on to the external reader.

Energy required for the acquisition and transmission of measurement values is supplied telemetrically between second transponder coil 2128 and the first coil 2114. In this case, first coil 2114 may be fixed to the sensor chip 2102. For the transmission of data from coil 2114 to an external reader, a sufficient telemetric range of the coil 2114 may be necessary and a hypodermic implantation of the coil 2114 at a suitable point of the patient's body may be required.

In one exemplary embodiment of the invention, both sides of the cardiac septum may be provided with one or more transponder coil antennas which are connected galvanically with wires or wireless via telemetry.

Figure 26:
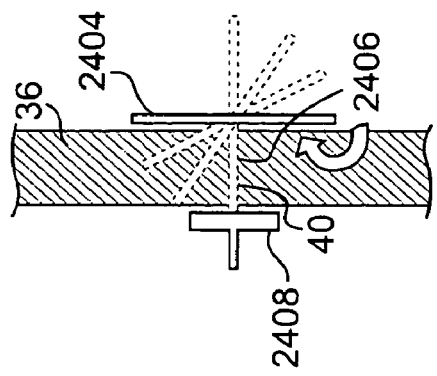
FIGS. 24, 25 and 26 schematically illustrate an embodiment of catheterization apparatus and general principles that may be employed in a minimally invasive method for implanting a telemetric measuring device according to principles of the invention.
Figure 25:
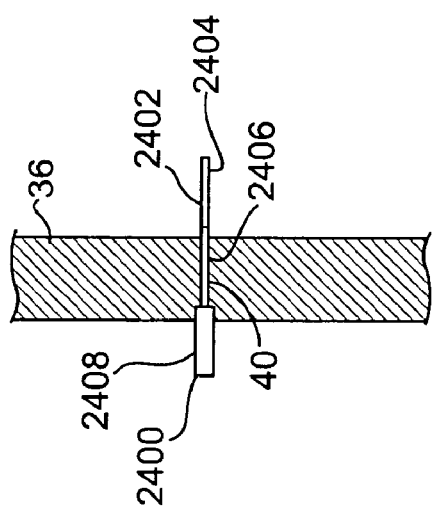
Figure 24:
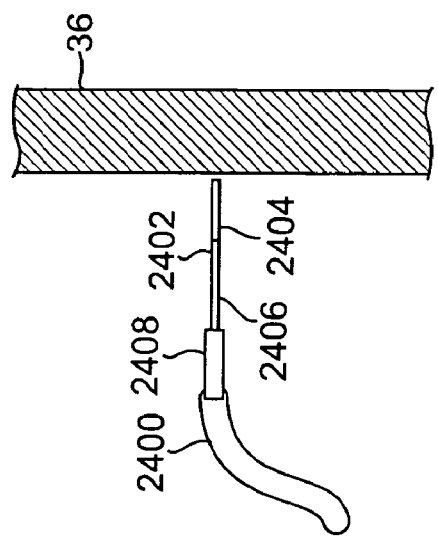

FIGS. 24, 25, and 26 schematically illustrate catheterization apparatus and three general principles—puncturing, inserting and implanting—that may be employed in a minimally invasive implantation method for implanting a telemetric measuring device according to principles of the invention. FIG. 24 illustrates puncturing the implantation site, such as the septum 36 of the heart. A conventional cardiac catheter 2400 may be used to deliver and position an implantable device 2402 of the invention within the cardiovascular system, such as the heart, of a patient. The implantable device 2402 includes a substantially rigid sensor chip 2404, a connection piece 2406 and an anchor structure 2408 of the invention, all shown in highly schematic fashion. The sensor chip 2404 includes an antenna (not shown). According to an embodiment of the invention, both the sensor chip 2404 and the anchor structure 2408 may be connected to the connection piece 2406 for selective longitudinal and pivotal or transverse movement, i.e. the sensor chip, anchor structure and connection piece may be longitudinally moved as a unit by or through the catheter, and the sensor chip and anchor structure may be selectively moved transversely or pivoted relative to the connection piece, as described below.

As illustrated in FIG. 25, the catheter is inserted through the septum 36 at the foramen 40 with the distal end of catheter 2400 initially located within the right atrium. The sensor chip 2404 may be configured to pierce the septum 36, e.g. may have a conical tip, such that moving the sensor chip 2404 distally punctures the septum 36 at the foramen 40.

As illustrated in FIG. 26, after the sensor chip 2404 pierces the septum 36 and passes into the left atrium, the connection piece 2406 is located within the foramen 40 of the septum 36. The anchor structure 2408 remains in the right atrium. The sensor chip 2404 may be moved or pivoted about its connection to the connection piece 2406 in any manner know in the art to occupy an expanded position against the interior surface of the septum 36 to secure the sensor chip 2404. Specifically, the sensor chip 2404 is then retracted in a proximal direction toward the doctor so that its surface contacts the interior of the septum 36. A portion of the connection piece 2406 fits within the foramen 40 of the septum 36. The anchor structure 2408 is simultaneously or subsequently moved or pivoted about its connection to the connection piece 2406 in any manner know in the art such that it is transverse to the longitudinal axis of the connection piece. The anchor structure 2408 is then positioned against the septum 36 and affixed to the connection piece 2406. The anchor structure 2408 and connection piece 2406 interact to attach the sensor chip 2402 to the septum 36 as disclosed above in FIGS. 21-22, for example.

FIGS. 27, 28, 29, 30, and 31 illustrate another embodiment of catheterization apparatus and more specific operational steps and structure that may be employed in another minimally invasive method for implanting telemetric measuring devices according to principles of the invention. According to an embodiment of the invention, the telemetric measuring device of the invention includes a collapsible anchor structure 2712, which may be formed from resilient arms that spring into an expanded position after release from the open, distal end 2718 of the catheter. By use of this anchor structure 2712, a sensor chip 2708 may be an ASIC as described herein or made of other, substantially rigid material that is not readily flexible, foldable or rolled. The anchor structure 2712 may be used to fix the sensor chip 2708 to a location at or near the cardiac septum 36. A portion of the anchor structure 2712 is placed within the foramen 40, as well as on both sides of the cardiac septum 36. Resilient arms 2714 of the anchor structure 2712, which may be formed from wire, will be disposed on both sides of the cardiac septum 36 after delivery (as shown in FIG. 32) to support the implanted sensor chip 2708. The apparatus and implantation steps will now be described in greater detail below.

Figure 27:
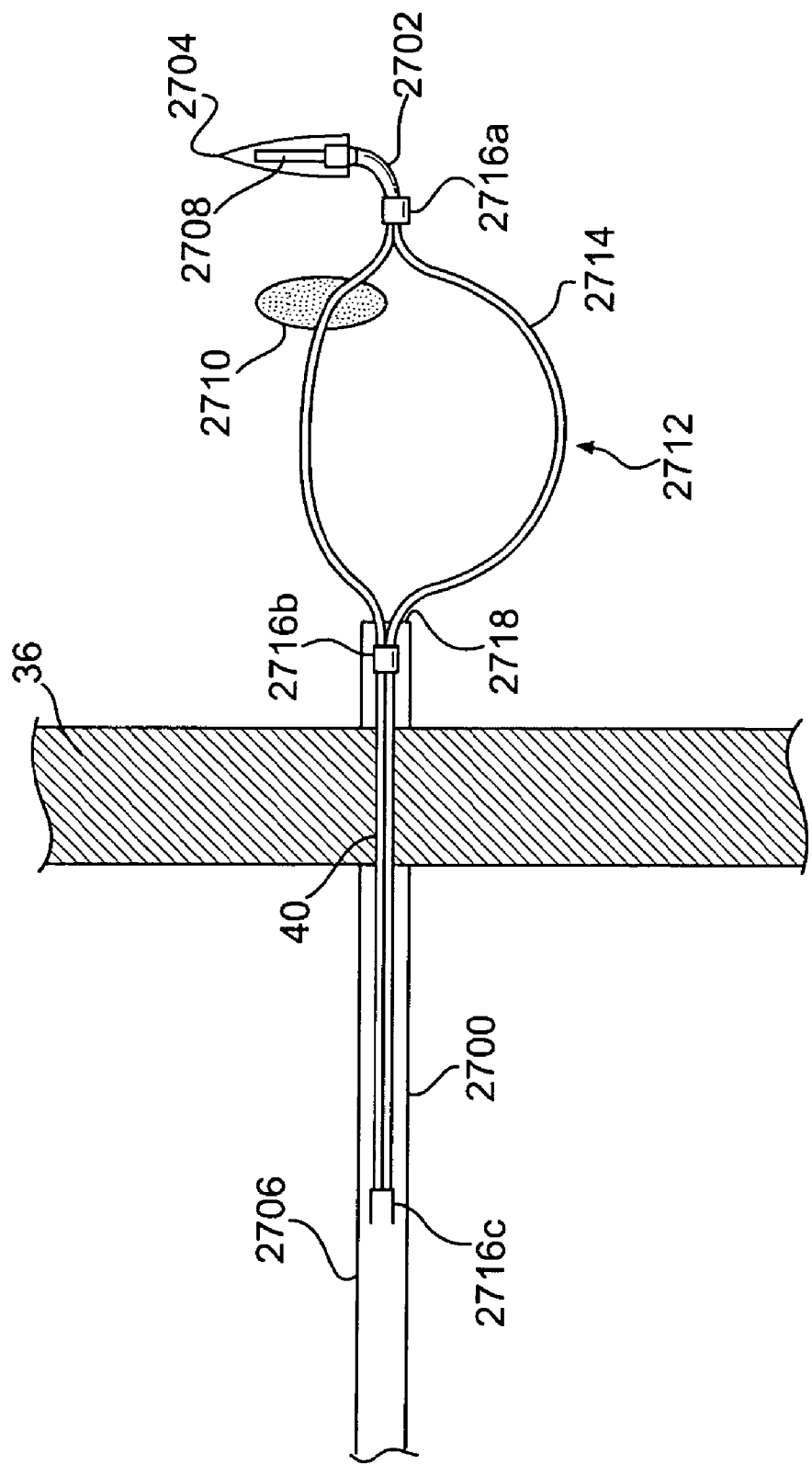
FIGS. 27, 28, 29, 30 and 31 schematically illustrate another embodiment of catheterization apparatus steps that may be employed in another minimally invasive method for implanting a telemetric measuring device according to principles of the invention.

With reference to FIG. 27, a telemetric measuring device is located within the lumen 2706 of a catheter 2700, which may be a conventional, cardiac catheter used to place medical devices within the cardiovasculature, including the heart. The sensor chip 2708 may be located within a conic end piece 2704 for piercing a heart wall such as septum 36. The sensor chip 2708 is located near the distal catheter opening 2718, while the anchor structure 2712 is folded into a collapsed position within the catheter lumen 2700, before it is delivered and implanted.

In general, the foramen 40 in the cardiac septum 36 may be effected artificially by inserting the tip 2704 of the catheter through the septum. The catheter 2700 is placed within the heart such that the distal catheter opening 2718 faces the septum 36. The conic end piece 2704 may be configured such that it is pushed through longitudinally and penetrates through the septum 36 and through foramen 40. The conic end piece 2704 may be encapsulated with a biocompatible sheathing and may be moved distally inward relative to the distal catheter opening 2718, after the opening 2718 passes into the chamber, such as the left atrium. Any means know in the art to effect such relative movement may be employed.

As discussed above, the anchor structure 2712 may be made of one or more looped, wired elements 2714 that normally occupy an expanded position, but are collapsible into a folded position fitting within lumen 2706. Anchor clips 2716a, 2716b, 2716c, such as quilled clips, may be used to attach together portions of the wired elements 2714 of the anchor structure 2712. Clips 2716a, 2716b, and 2716c are attached prior to delivery. The wired elements 2714 may be self-expanding support units made of synthetic material. For example, a metal with a shape memory, such as nitinol, may be used, so that the wired elements 2714 expand to their original shape upon deployment from the end of the catheter. The anchor structure 2712 is designed to be compressed within the catheter lumen 2706 during delivery.

Figure 28:
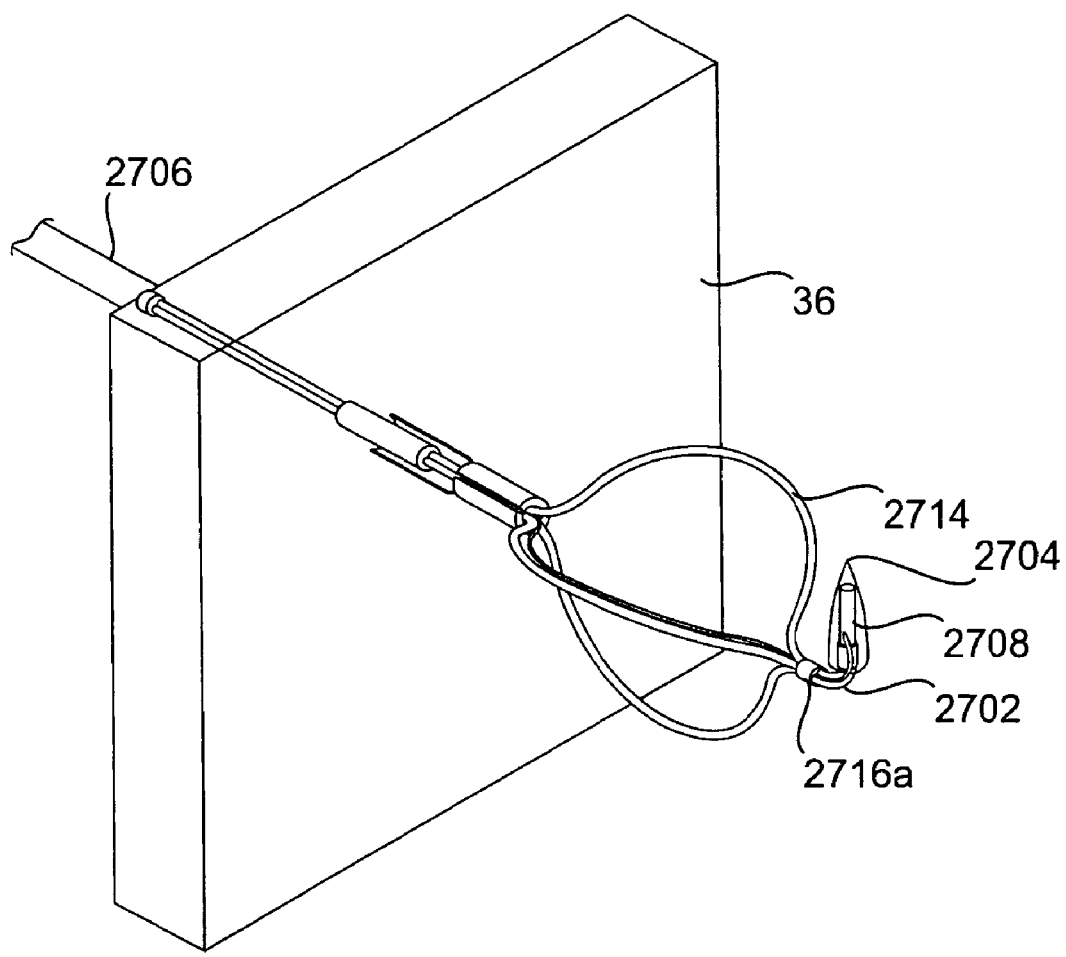

As illustrated in FIGS. 27 and 28, after distal catheter end 2718 and the sensor chip 2708 are inserted through the septum 36, the anchor structure 2712 also is inserted through the septum 36 such that anchor clip 2716a is located beyond the septum 36 and in the heart chamber, but clip 2716b remains in the lumen 2706. The wire arms 2714 are now free and deploy towards their normally expanded positions.

Figure 29:
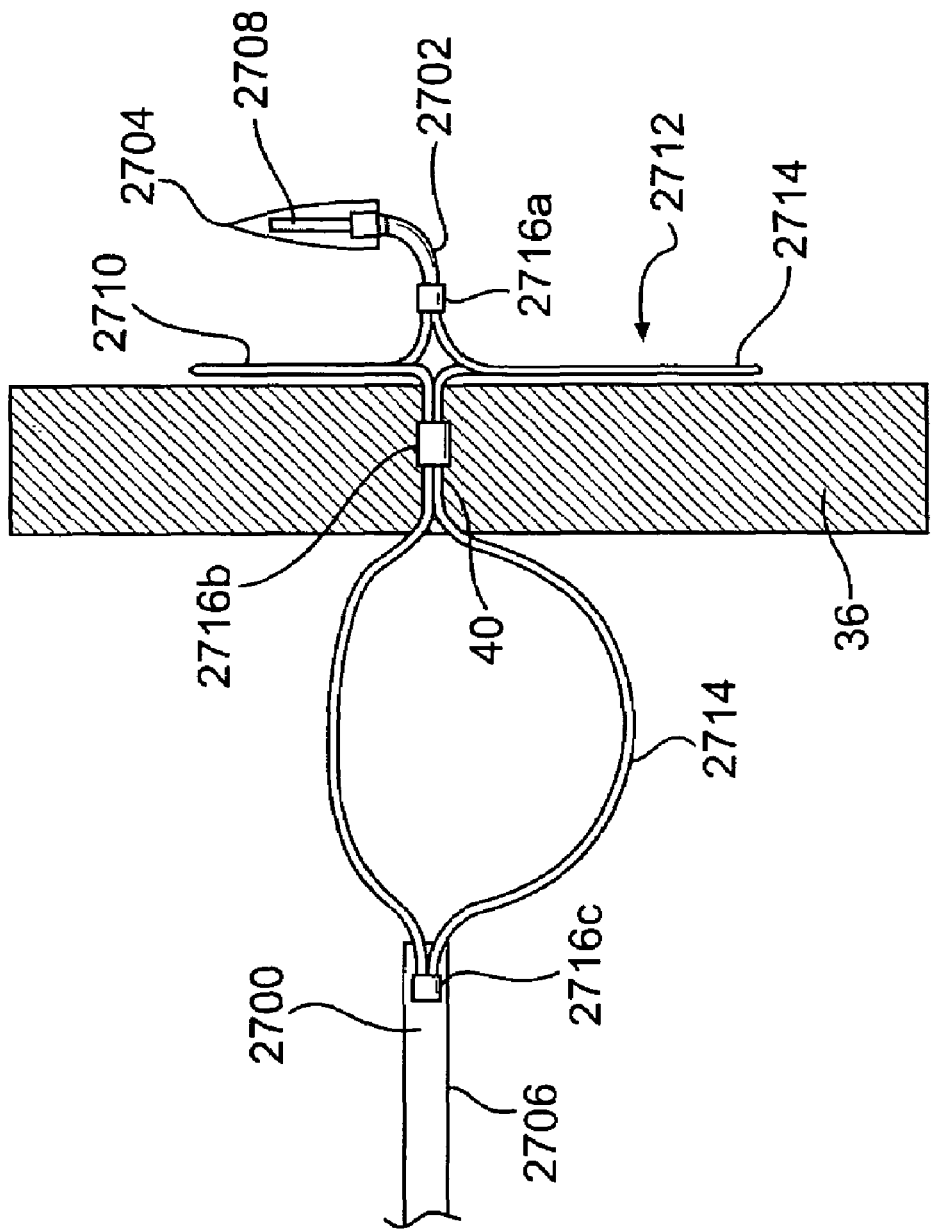
Figure 30:
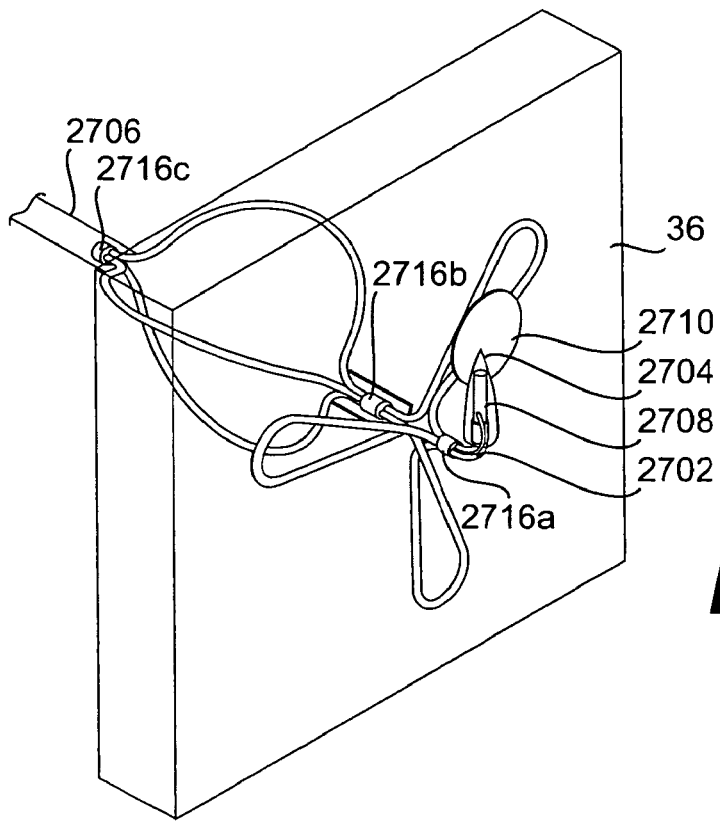

As illustrated in FIGS. 29 and 30, the catheter lumen 2706 is then pulled back proximately through and out of the foramen 40. This also pulls the sensor 2708 and the wire arms 2714 proximally, which expand to their original shape and contact the inner surface of the septum 36. In the embodiment illustrated in FIGS. 29 and 30, an antenna 2710 is located on one of the three wire arms 2714 that contact the septum 36, i.e. the antenna 2710 is on the same side of the septum 36 as the sensor chip 2708.

Further, the implantable clip 2716b, which also engages the wire elements 2714, is pulled into the foramen 40. Proximal portions of the three wire arms 2714 between clips 2716b and 2716c also are deployed out of the catheter lumen 2706 as the catheter is further retracted, although clip 2716c and the remaining portions of the wire elements 2714 may remain within the catheter lumen 2706 at this time. The wire elements 2714 on the proximal, outer side of the septum 36 opposite the sensor chip 2708 are now deployed and begin to regain their original, expended shape as shown in FIGS. 29 and 30.

Figure 31:
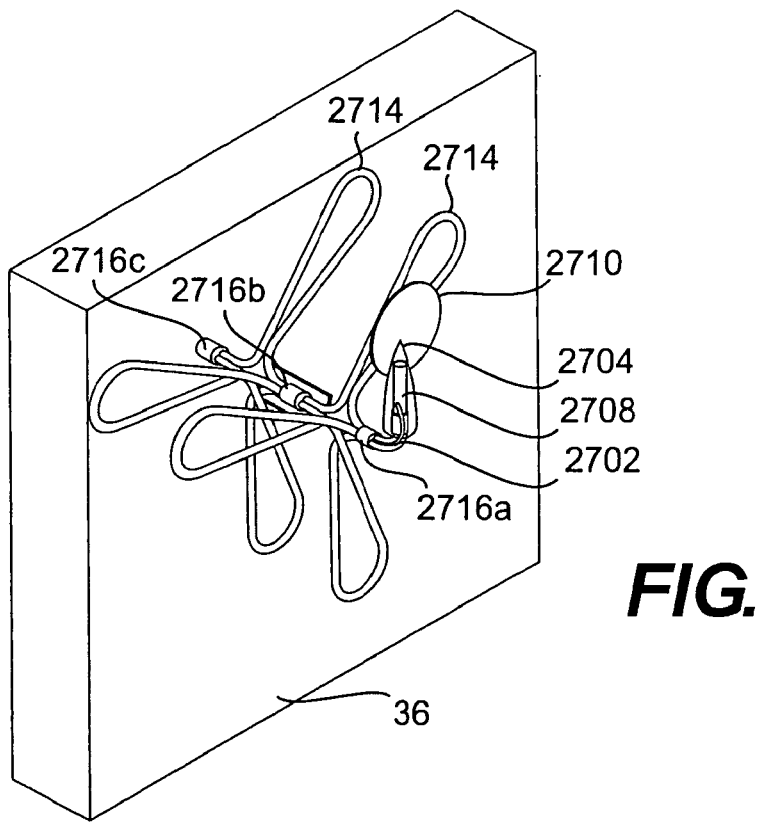
Figure 32:
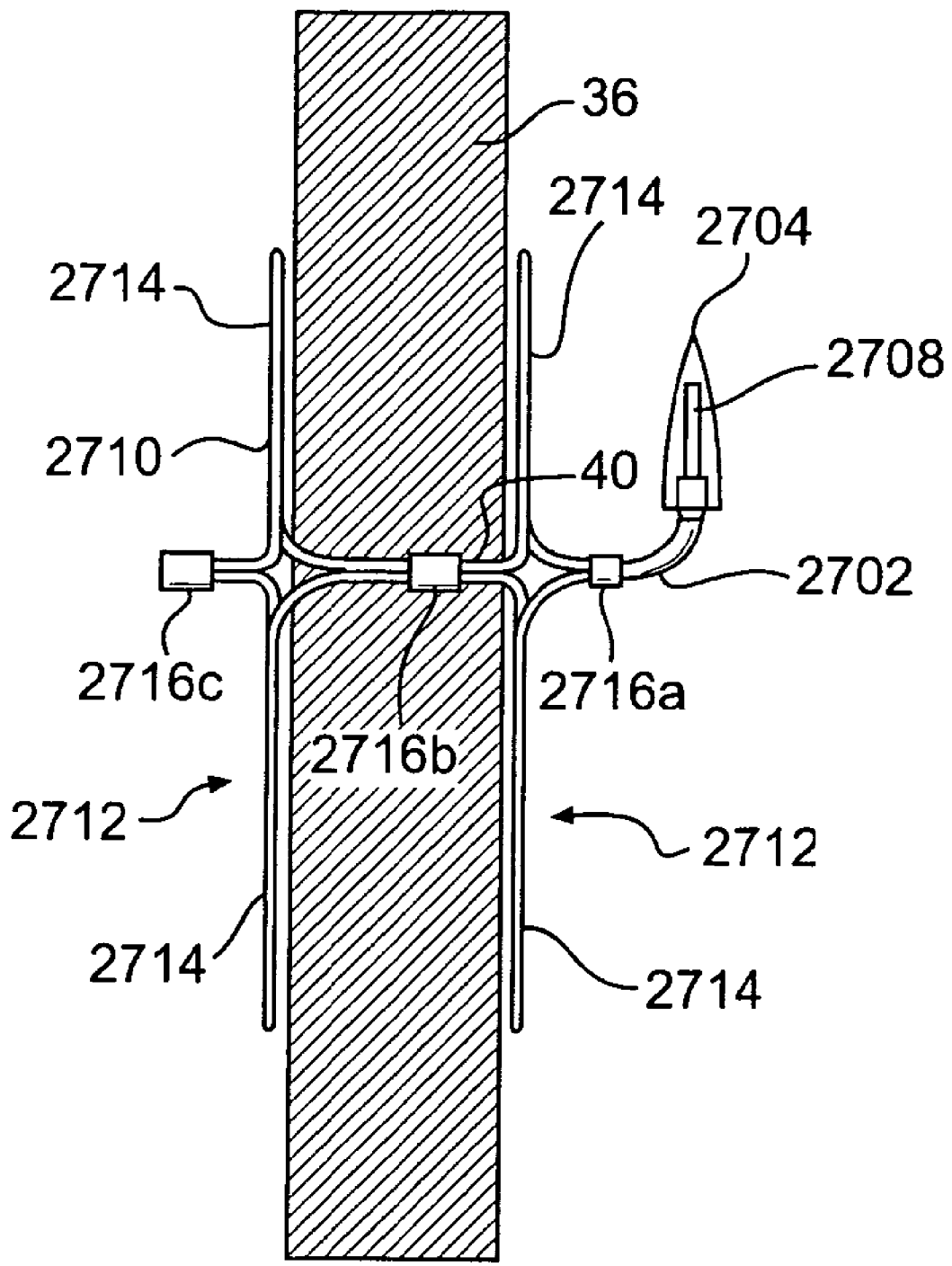
FIGS. 32 and 33 illustrates another embodiment of an implantable telemetric measuring device for use in the catheterization method described in FIGS. 27, 28, 29, 30, and 31.

FIG. 31 illustrates the telemetric measuring device implanted in position and attached to the septum 36, after the catheter has been removed from the device, by any means known in the art. The wire arms 2714 on both sides of the septum 36 have regained their expanded shape and contact the walls of the septum 36, with the intermediate portion of the wire elements 2714 located within the foramen 40 in a collapsed position held by clip 2716b. A sensor fastener 2702 such as a bend or elbow supports the sensor chip 2708 within the left atrium 34 and away from the heart itself, and particularly the septum 36. Thus, the design of the anchor structure 2712 allows the implantation of the sensor chip 2708 into the left atrium. The antenna structure 2710 may be located on the surface of the wired elements 2714 of the anchor structure 2712. Blood pressure can act directly on the pressure sensors (not shown) of the sensor chip 2708. Thus, the sensor fastener 2702 of the anchor structure 2712 attaches the sensor chip 2708 to the anchor structure 2712 and places the sensor chip 2708 away from the septum 36. The cardiac motion, especially the motion of the cardiac septum, will have reduced or no significant, deteriorating effect on the sensor chip 2708 and, therefore has less or no significant influence on the quality of measurement results. This may also be due to the design of the substantially rigid sensor, such as an ASIC as described above, in which the pressure sensors are housed. This enables only the actual blood pressure values to be measured and obtained by the sensor chip 2708. Mismeasurements or negative reports which may occur with conventional, flexible pressure measuring devices can be avoided.

Figure 33:
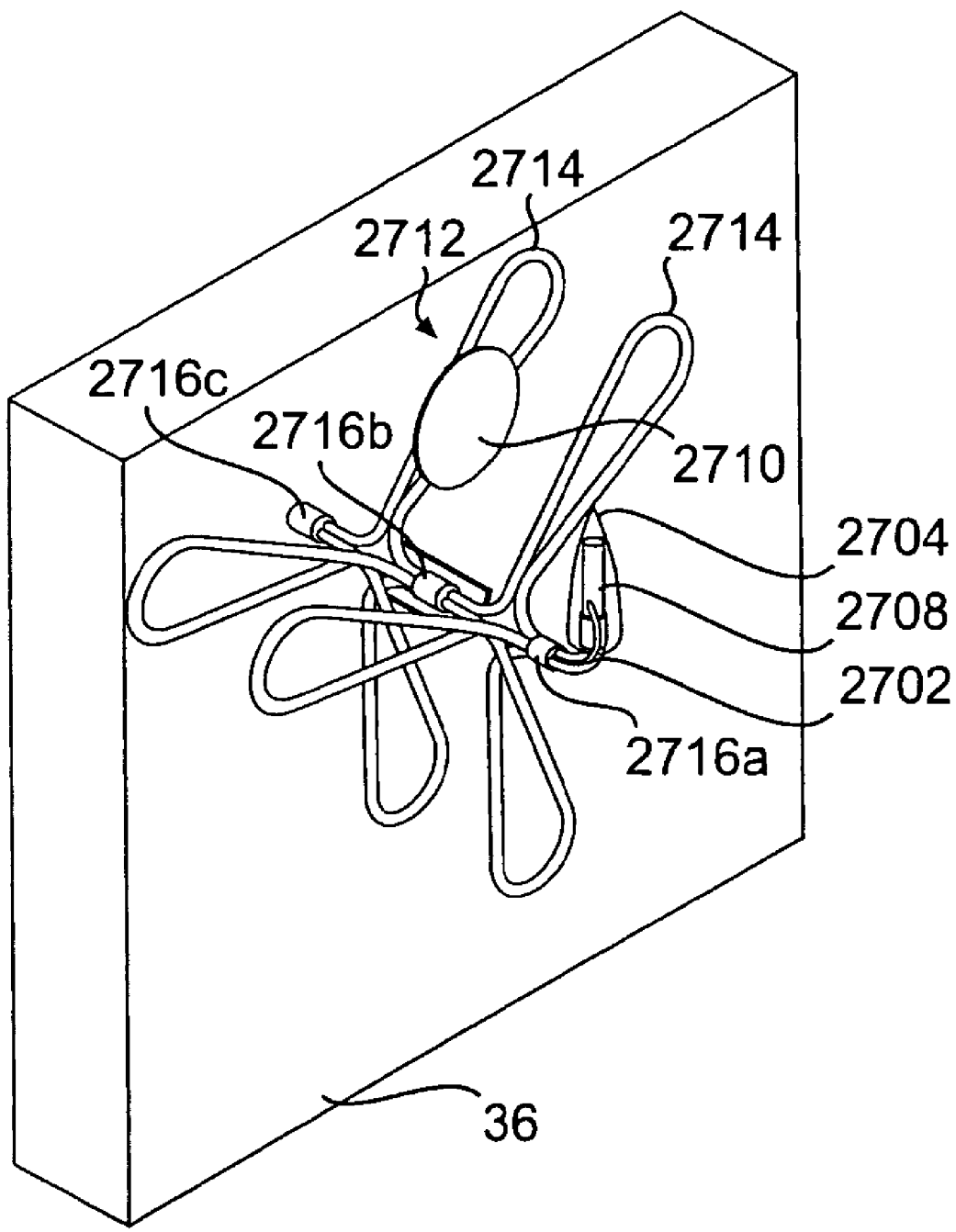

FIGS. 32 and 33 illustrate another embodiment of an implantable telemetric measuring device of the invention for use in the method described in FIGS. 27, 28, 29, 30, and 31. More specifically, the embodiment of FIGS. 32 and 33 illustrates the implantable device affixed to the septum 36, but with the antenna 2710 located on the side of the septum 36 opposite the sensor chip 2708. According to an embodiment of the invention, electrical conductive wires (not shown) may be located in the foramen 40 and connect the antenna device 2710 with the sensor chip 2708. Alternatively, the sensor chip 2708 may have an internal coil that telemetrically communicates with antenna 2710. Other configurations may also be used as the skilled artisan will recognize.

With its generally oblong shape, the sensor chip 2708 may be optimized for catheter implantation methods. The diameter of the sensor chip 2708 may be adapted to the typical size of the foramen 40 in the cardiac septum 36.

During the implantation process, the antenna 2710, which is folded or rolled up, may be arranged lengthwise to the oblong form of the sensor chip 2708. Antenna 2708 and sensor chip 2708 also may be connected via an electroconductive connection piece.

The implantable device may be designed in such a way that other types of physical values can also be measured e.g. the blood temperature at the place of implantation. Both values, blood pressure and blood temperature, may be measured either co-instantaneously or asynchronously.

Figure 34:
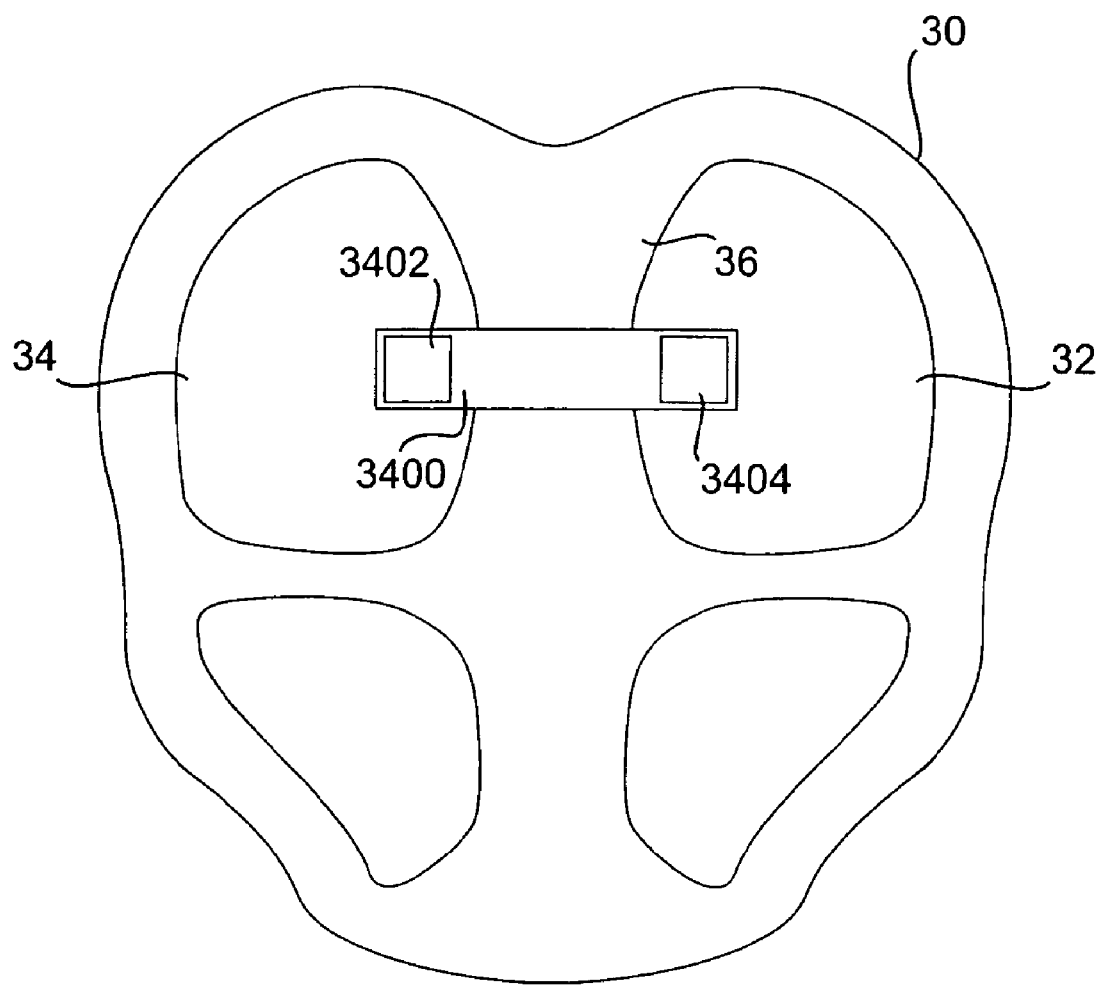
FIG. 34 schematically illustrates the placement of a multiple-heart chamber sensor chip constructed according to principles of the invention.

According to another embodiment of the invention, the implantable sensor chip of the invention may sense conditions in more than one chamber of the heart. FIG. 34 illustrates the placement of a multiple, heart chamber sensing device 3400 of the invention. Sensor chip 3400 is implanted in the septum 36 of the heart 30 surgically or via catheterization, e.g. using the technique described herein. The sensor chip 3400, such as an ASIC, has a first pressure sensing portion 3402, having pressure sensors, located in the right atrium 34 and a second pressure sensing portion 3404, having pressure sensors located in the right atrium 32. Alternatively, two or more chips may be connected via a wire and positioned to achieve sensing in two or more chambers. The data could then be transmitted to an external reader using appropriate protocols, in accordance with the invention.

Figure 35:
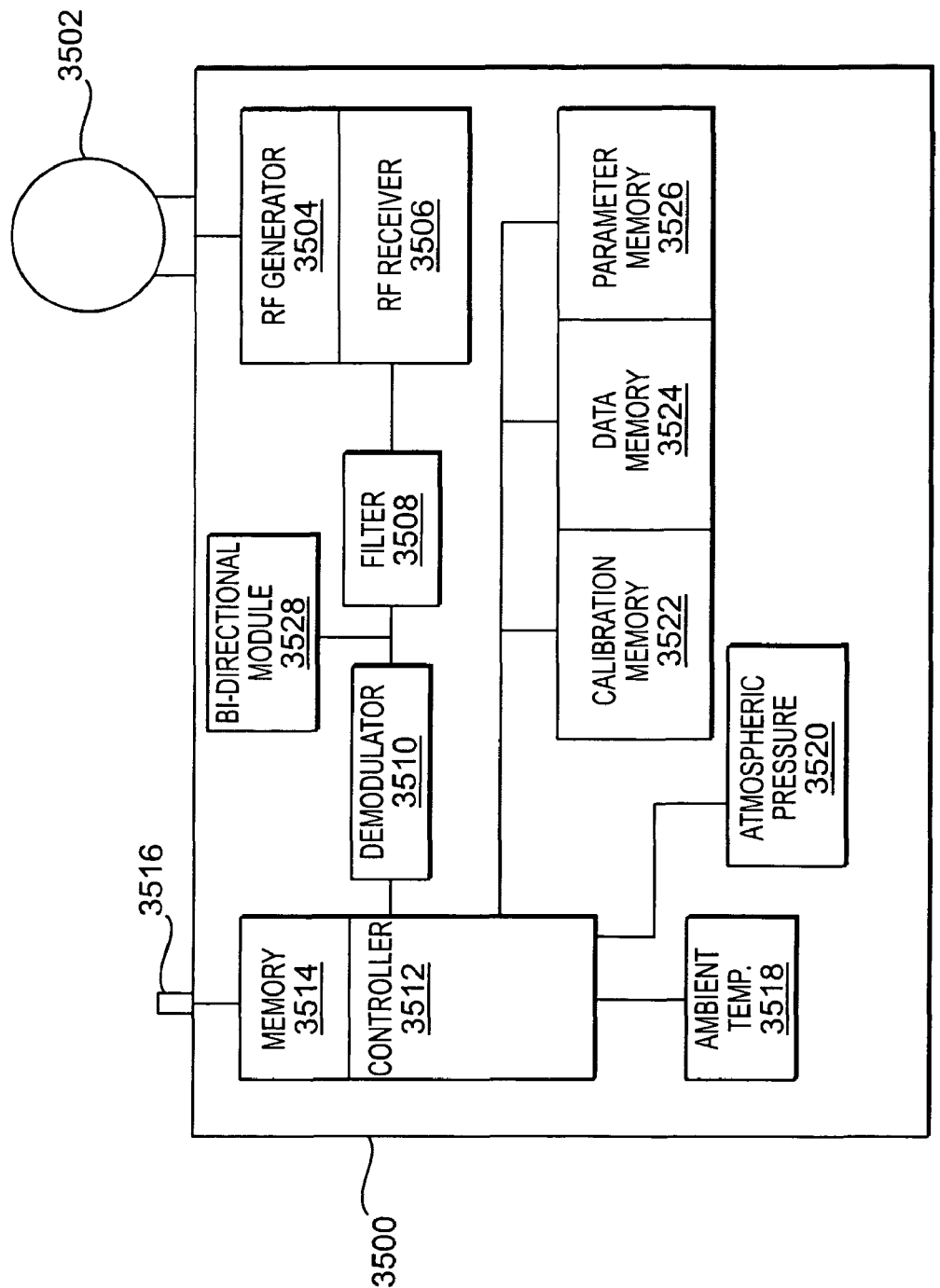
FIG. 35 is a block diagram of the major electronic components of an external reader constructed according to the principles of the invention for telemetrically receiving data from an implanted sensor chip.

FIG. 35 is a block diagram of the major electronic components of an external reader 3500 of the invention for telemetrically receiving data from an implanted sensor chip. An antenna 3502 may be integrated with the external reader 3500, as shown schematically in FIGS. 1-2. Also, as illustrated in FIG. 1, the external reader 12 may be attached to the patient, or alternatively, as illustrated in FIG. 2, the external reader 26 may be incorporated inside a handheld device. In other cases, the antenna 3502 may be attached to the patient's body or connected to the external reader 3500 by cable connections. Another method attaches the external reader to the patient's bed or seat. Numerous such arrangements may be employed to adapt to the particular application, as the skilled artisan will recognize.

The antenna 3502 is used for receiving data, in the form of digital signals, from the implanted sensor chip. The digital signals are received at the RF receiver 3506 via an RF generator 3504. The RF generator 3504 generates an RF signal to be transmitted via the antenna 3502 to power the implanted device.

The digital data signals received by RF receiver 3506 are processed by filter 3508 and demodulator 3510 before being received and then processed as appropriate by controller 3512. A bidirectional power module 3528, described in detail below, is connected between the filter 3506 and demodulator 3510. Separate memory devices, such as calibration memory 3522, data memory 3524, and parameter memory 3526, may be provided and communicate with controller 3512. The calibration memory 3522 stores calibration information associated with a particular ASIC sensor system, and the calibration memory 3522 may store calibration information for a number of different ASIC sensor systems. Calibration information may be obtained from an external source, such as a computer, through communications port 3516. The appropriate calibration information, based on a unique identification number of the ASIC sensor system being interrogated, is obtained from the calibration memory 3522. Thus, a medical professional, such as a doctor or nurse, can use one reader to obtain pressure readings from multiple patients.

The data memory 3524 stores data related to the pressure and/or temperature received from the ASIC of the implanted sensor chip. The data may be stored in the data memory 3524, and then transferred, via a data memory module 3514, to another device through data communications port 3516, such as a computer. Using information obtained from an atmospheric pressure module 3520, the controller 3512 uses the data received from antenna 3502 and stored in data memory 3524 to determine the pressure within the heart, as is known in the art. Using the information from the ambient temperature module 3518, the controller 3512 also uses the data to determine the temperature within the heart, as is known in the art.

The pressure and temperature calculations, which are performed in controller 3512, as well as the data from the implanted sensor chip, may be stored in the data memory module 3514. These calculations and data may then be communicated to another device, such as a computer through communications port 3516.

The pressure sensor readings, and the parameter alerts described below, may be displayed by the reader on a display (not shown), such as an LCD display or the like. The measured pressure values and parameter alerts also may be displayed on a monitor of the external reader (not shown) and recorded in an appropriate storage device. The system may be equipped for purposes of telemedicine, so that data is transmitted from the external reader to a medical department or healthcare provider via wire connection, telephone, internet or any other suitable telecommunication source is possible, via known wired or wireless protocols.

The parameter memory 3526 stores parameter thresholds. The data received from the implanted sensor chip is compared by the controller 3512 to the parameter thresholds. If the data fails to meet a particular threshold, or exceeds a particular threshold, an alarm may occur to alert a user. The threshold parameters may be set by a doctor or other health care professional. By way of example, the threshold range for pressure may set to 25 to 30 mm Hg, depending on the patient. If the reader receives a measurement of 25 mm Hg, which is above the threshold range, it alerts the user that the measurement exceeds the threshold. Further, an alert may occur based on the raising of pressure per time. Other parameters may also be used.

The parameter thresholds may be provided to the external reader 3500, such as by a user manually entering a parameter threshold. Alternatively, the parameter thresholds may be provided to the external reader 3500 from another device, such as computer through communications port 3516. The parameter thresholds may be provided via a direct connection, such as by a wire, or by a wireless connection, such as by a LAN, a WAN or the like.

The calibration memory 3522, the data memory 3524 and the parameter memory 3526 may be separate memory storage devices within the external reader, or each may be a portion of a single memory storage device. The reader may use a signal at 13.56 MHz, or other known frequencies. One example of a suitable reader is disclosed in published patent application No. PCT/EP2004/012670.

Bi-directional power evaluation module 3528 assists in evaluating the strength of signals received from the implanted device to ensure that a minimum signal strength is received. The signal received from the implanted devices via antenna 3502 is evaluated by the bi-directional power evaluation module 3528. The evaluation may be implemented via various methodologies. According to an embodiment of the invention, the reader may increase the power of the signal sent via the antenna 3502 to the implanted device over small increasing increments. At each increment, the bi-directional power evaluation module 3528 evaluates the signal received back from the implanted device to determine the quality and strength of the signal. This process is repeated until a successful signal is received from the implanted device. The reader than uses the minimum power necessary to achieve an acceptable signal and begins performing the reading of data, such as pressure and temperature measurements, from the device. This may be performed by taking a predetermined number of readings (e.g., five readings) in a row. All the readings may be taken after the minimum power level has been determined. Alternatively, the bi-directional power evaluation module 3528 may determine the minimum power level after each of the predetermined readings.

By way of another embodiment of the invention, the reader can increase the power level supplied by the antenna 3502 by larger increments, such as by quarter Fourier steps (FS steps), until a valid signal is received from the implanted device. Once a valid signal is obtained, the power is decreased by one step, such as ¼ FS, then increased in smaller steps, such as ⅛ FS steps) until a valid signal is received. This process is repeated using progressively smaller steps (1/16 FS, 1/32 FS) until a minimum power level is determined. The reader then uses the resulting minimum power level to compute the required power setting and obtains a predetermined number of readings.

Another methodology involves assessing the demodulation quality level (DQL) of the signal in addition to the signal state analysis described above. The DQL of a signal changes as the coil geometry and/or distance from the reader changes. It does not use an incremental algorithm to assess the required starting power, but the last power setting of the last measurement. The reader sets the power to a previously used level. If a reading is possible, the reader increases or decreases the power for the next reading according to DQL. If no reading is possible, the reader increases the power in increments until valid signal is received from the implanted device. After a predetermined number (e.g., five) of successful readings, the reader obtains the measurement readings. During these measurement readings, the reader continues to increase, decrease, or hold the power level according to DQL and obtaining valid signals.

Use of power conditioning may result is various beneficial characteristics and features for the voltage controller/stabilizer supply voltage ($V_{DDA}$) used in the ASIC. When using power conditioning, there is generally a high common mode rejection ratio (CMRR) for $V_{DDA}$, as well as good radio frequency (RF) suppression for $V_{DDA}$. In addition, a fast power on reset (POR) signal is used if $V_{DDA}$ falls below tolerance, which would happen if supply power is not sufficient. Because there is no measurement or signal transmission if POR not "1," determining a proper power supply using the power conditioning may prevent this drawback.

The implantable sensor chip of the invention also may be incorporated or attached to other devices implanted within the body. Examples of such devices may include a pacemaker, defibrillator or a drug dispenser.

While the invention has been described in terms of exemplary embodiments, those skilled in the art will recognize that the invention can be practiced with modifications in the spirit and scope of the appended claims. For example, while the embodiments described above have been directed to implantation of the telemetric sensing device of the invention within the heart, one or more such devices may be implanted within other positions in the cardiovascular system of a patient, such as the aorta, pulmonary artery, or any of the other great vessels. These examples given above are merely illustrative and are not meant to be an exhaustive list of all possible designs, embodiments, applications or modifications of the invention.

The invention claimed is:

1. An implantable pressure monitor comprising:
   a sensor assembly comprising:
      a substantially rigid chip including:
         a proximal end and a distal end;
         pressure sensors exposed on a first surface of the chip in a sensor region of the distal end;
         signal processing circuitry receiving pressure-indicative signals from the sensors and producing pressure-indicative output signals; and
         a chip electrical connector in the proximal end communicating the output signals;
      a substantially rigid substrate that:
         is spaced apart from the chip;
         faces the first surface of the chip;
         is connected to the chip electrical connector in the chip's proximal end by a substrate electrical connector;
         defines an aperture positioned over the sensor region of the chip's distal end, thereby exposing the pressure sensors; and
         covers the distal end of the chip except for the sensor region; and
      a flexible filler material located throughout space between the chip and the substrate except beneath the aperture, thereby leaving the pressure sensors exposed, such that (a) the flexible filler material connects the chip to the substrate, and (b) the distal end of the chip is connected to the substrate by only the flexible filler material;
   a wire that:
      extends from the substrate;
      is electrically connected to the substrate electrical connector;
      communicates the output signals; and
      is not connected to the chip;
   a biocompatible sheath that encapsulates the sensor assembly and wire and is sufficiently flexible to transmit pressure exerted on the sheath exterior through the sheath;
   a pressure-transferring medium extending from the sheath, through the aperture, and to the pressure sensors, thereby transferring pressure exerted on the sheath exterior to the pressure sensors;
   an anchor structure that is:
      sized and shaped for securing the implantable pressure monitor to an anatomic structure; and
      foldable to fit within a delivery catheter lumen; and
   a sensor fastener holding the sensor assembly away from the anchor structure.

2. The implantable pressure monitor of claim 1, wherein the sensor fastener comprises a bend or an elbow shape.

3. The implantable pressure monitor of claim 1, wherein the sheath has a curved shape to reduce or eliminate hydrodynamic forces.

4. The implantable pressure monitor of claim 1, wherein the substantially rigid substrate extends distally from the chip to a distal end which comprises a barrier wall protecting a distal end of the chip.

5. The implantable pressure monitor of claim 4, wherein the barrier wall forms an end cap at the distal end of the chip.

6. The implantable pressure monitor of claim 5, wherein the barrier wall extends in a direction substantially perpendicular to a plane of the substrate and to a height such that a top of the barrier wall is at or above a top of the chip.

7. The implantable pressure monitor of claim 4, wherein the substantially rigid substrate further extends distally from the barrier wall to a tapered front portion.

8. The implantable pressure monitor of claim 1, wherein the sheath comprises a one-piece, seamless silicone covering.

9. The implantable pressure monitor of claim 1, wherein the pressure-transferring medium comprises silicone.

10. The implantable pressure monitor of claim 1, wherein the anchor structure comprises resilient arms that spring into an expanded position after release from confinement.

11. The implantable pressure monitor of claim 10, wherein the resilient arms of the anchor structure are arranged as two looped wire elements separated by a distance corresponding to or slightly less than the thickness of a cardiac septum, and the sensor assembly is positioned outside the anchor structure.

12. The implantable pressure monitor of claim 1, wherein the substrate is sufficiently rigid such that it cannot be folded or rolled up.

13. The implantable pressure monitor of claim 1, wherein the substrate is sufficiently rigid to protect the pressure sensors from damage as a consequence of contact with a surgical instrument during implantation and from mechanical damage during use.

14. The implantable pressure monitor of claim 1, wherein the substantially rigid substrate is sufficiently rigid to protect the pressure sensors from damage due to stress and strain due to bending of the monitor during insertion.

15. The implantable pressure monitor of claim 1, wherein the substrate is sufficiently rigid to avoid twisting of the chip due to turbulent blood flow.

16. The implantable pressure monitor of claim 1, wherein the substrate is rigid.

17. The implantable pressure monitor of claim 1, wherein the substrate is mechanically inflexible.

18. The implantable pressure monitor of claim 1, wherein the flexible filler material comprises silicone.

19. The implantable pressure monitor of claim 1, wherein the flexible filler material holds the chip and the substrate together in a fixed relationship.

* * * * *